United States Patent [19]

Zinreich et al.

[11] Patent Number: 5,474,569
[45] Date of Patent: Dec. 12, 1995

[54] POST-SURGICAL GROSS PATHOLOGY SPECIMEN MARKER

[75] Inventors: Simion J. Zinreich; Eva S. Zinreich, both of Owings Mills, Md.; Rex O. Bare, Lake Forest; Robert D. Miller, Costa Mesa, both of Calif.

[73] Assignee: Izi Corporation, Owings Mills, Md.

[21] Appl. No.: 117,487

[22] Filed: Sep. 7, 1993

Related U.S. Application Data

[63] Continuation of Ser. No. 853,505, Mar. 18, 1992, abandoned.

[51] Int. Cl.⁶ .................................................. A61B 19/00
[52] U.S. Cl. .................................................. 606/151
[58] Field of Search .............. 24/357, 362, 710.6–710.8; 606/116, 117, 1, 138, 139, 151, 157, 213, 216–221, 228, 232, 142, 144, 158; 227/901, 902; 40/300–302

[56] References Cited

U.S. PATENT DOCUMENTS

| 149,485 | 4/1874 | Kingman . | |
|---|---|---|---|
| 367,611 | 8/1888 | Winnek | 24/710.8 |
| 2,443,372 | 6/1948 | Bertram . | |
| 2,869,338 | 1/1959 | Norgaard et al. . | |
| 3,067,534 | 12/1962 | Paxton . | |
| 3,320,958 | 5/1967 | Nolan | 606/158 |
| 3,334,434 | 8/1967 | Melin . | |
| 3,802,437 | 4/1974 | Kees | 606/158 |
| 3,955,580 | 5/1976 | Thompson . | |
| 4,041,931 | 8/1977 | Elliott et al. | 606/151 |
| 4,121,591 | 10/1978 | Hayes . | |
| 4,195,635 | 4/1980 | Ritchey . | |
| 4,506,669 | 3/1985 | Blake | 606/218 |
| 4,526,174 | 7/1985 | Froehlich | 606/219 |
| 4,535,772 | 8/1985 | Sheehan | 606/217 |
| 4,983,176 | 1/1991 | Cushman et al. | 606/216 |
| 5,242,456 | 9/1993 | Nash et al. | 606/142 |

FOREIGN PATENT DOCUMENTS

| 0122046 | 10/1984 | European Pat. Off. | 606/221 |
|---|---|---|---|
| 0790997 | 11/1935 | France | 606/218 |
| 0178418 | 5/1954 | Germany | 606/221 |

Primary Examiner—Stephen C. Pellegrino
Assistant Examiner—Glenn Dawson
Attorney, Agent, or Firm—Lyon & Lyon

[57] ABSTRACT

A set of post-surgical gross pathology specimen marking devices which may be used to identify various surfaces of pathology specimens is presented. The device includes a set of pathology specimen markers which are releasably attached to a holder. The markers disclosed are of various shapes and designs, and each includes a gripper element. The markers are designed such that the gripper element may be manipulated to allow a portion of a pathology specimen to be pinched, pierced, or clipped by the gripper element thereby attaching the marker to the specimen. The markers are designed so they may be manipulated by using a tool (such as forceps) to attach the specimen marker to a pathology specimen in a matter of seconds.

6 Claims, 32 Drawing Sheets

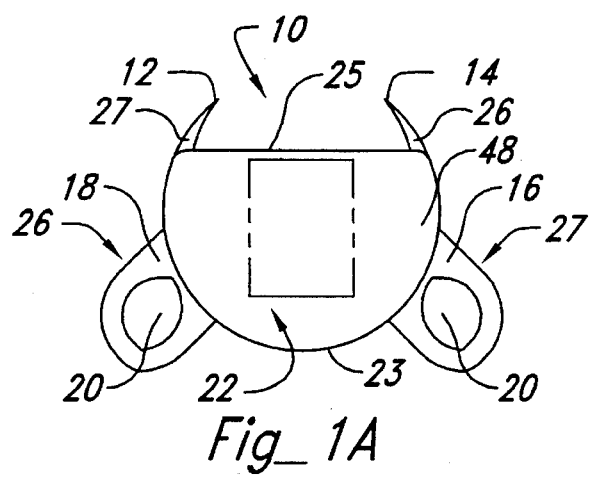
Fig_1A
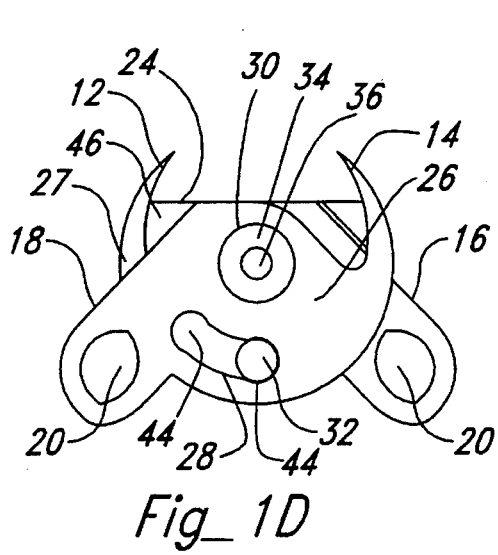
Fig_1D
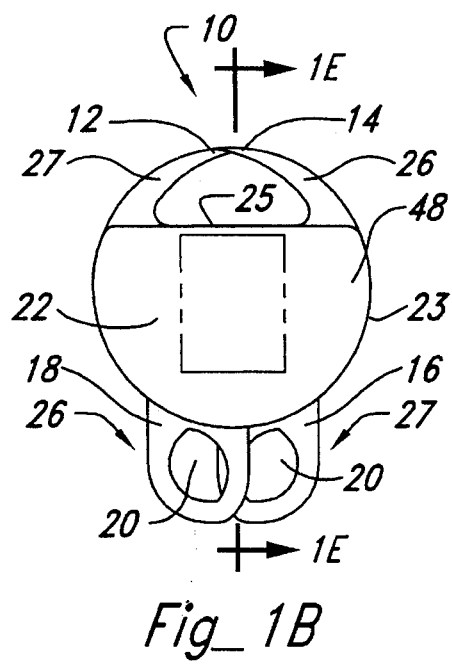
Fig_1B
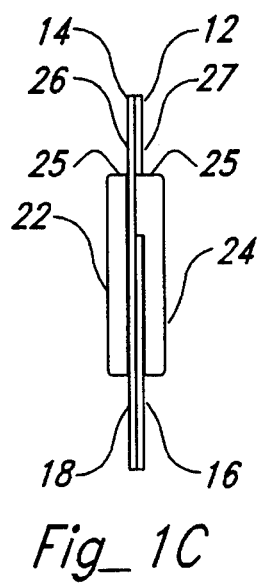
Fig_1C
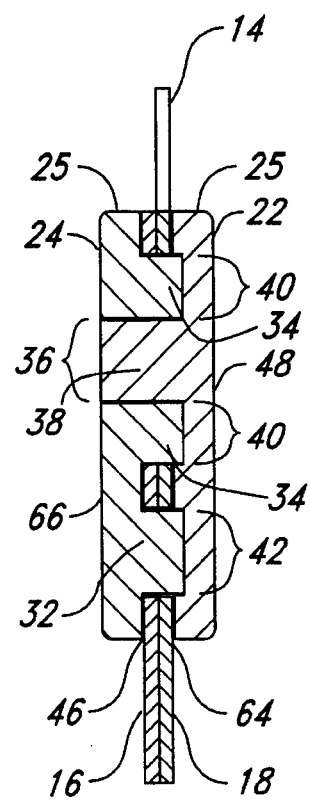
Fig_1E

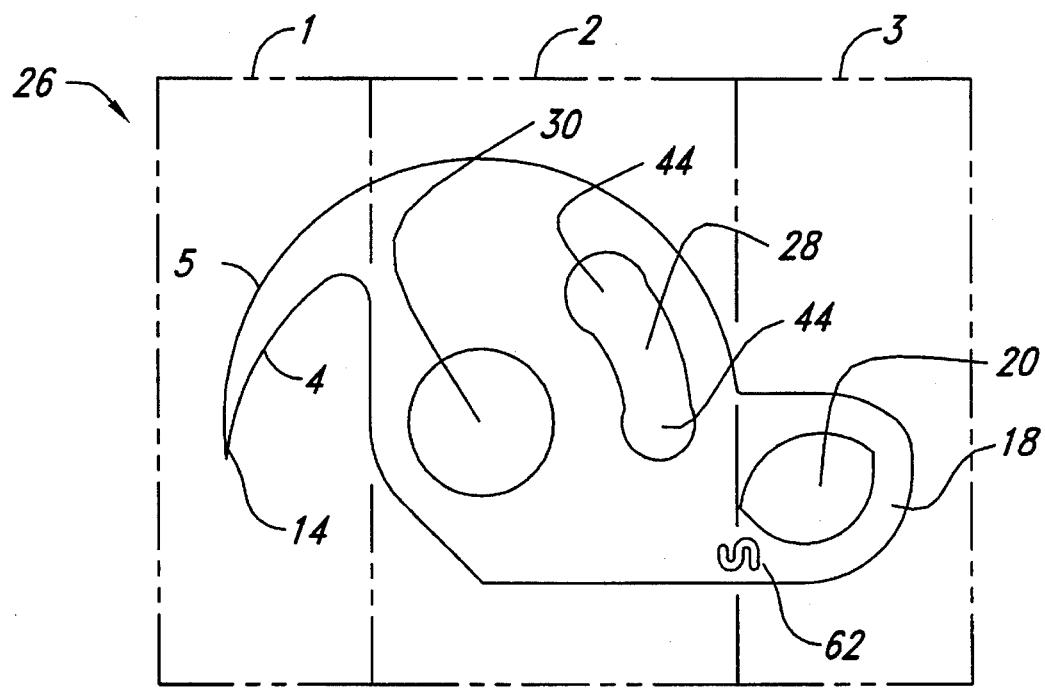
Fig_1F
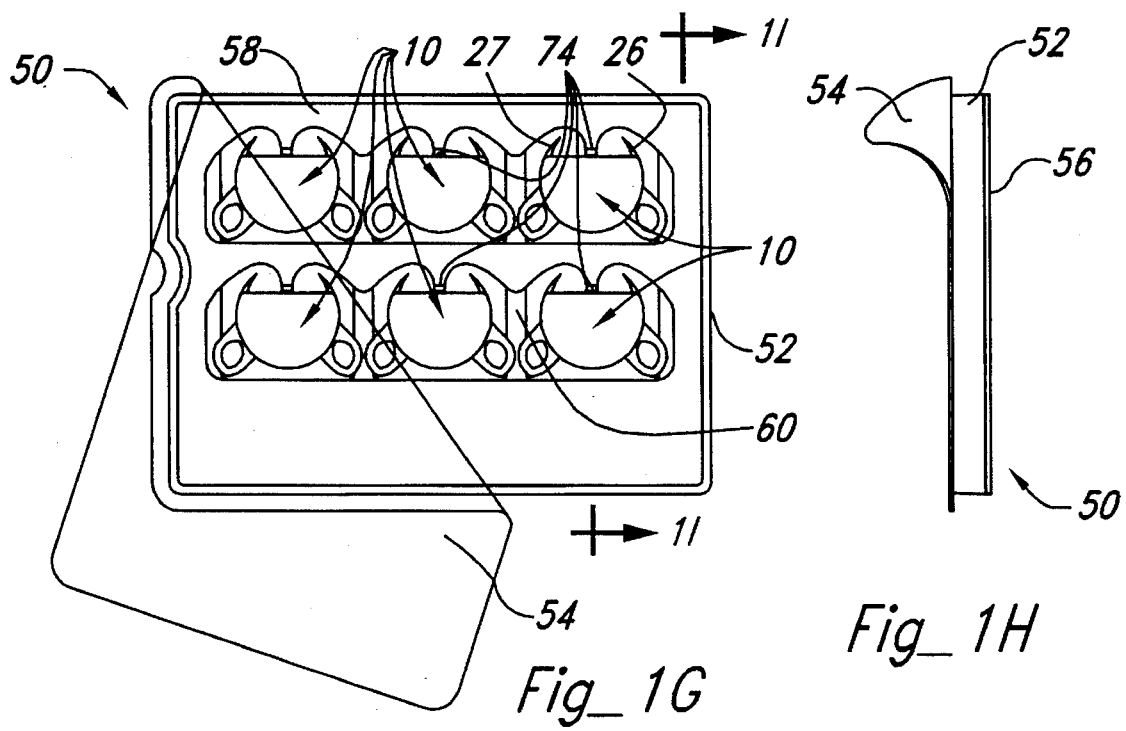
Fig_1G
Fig_1H

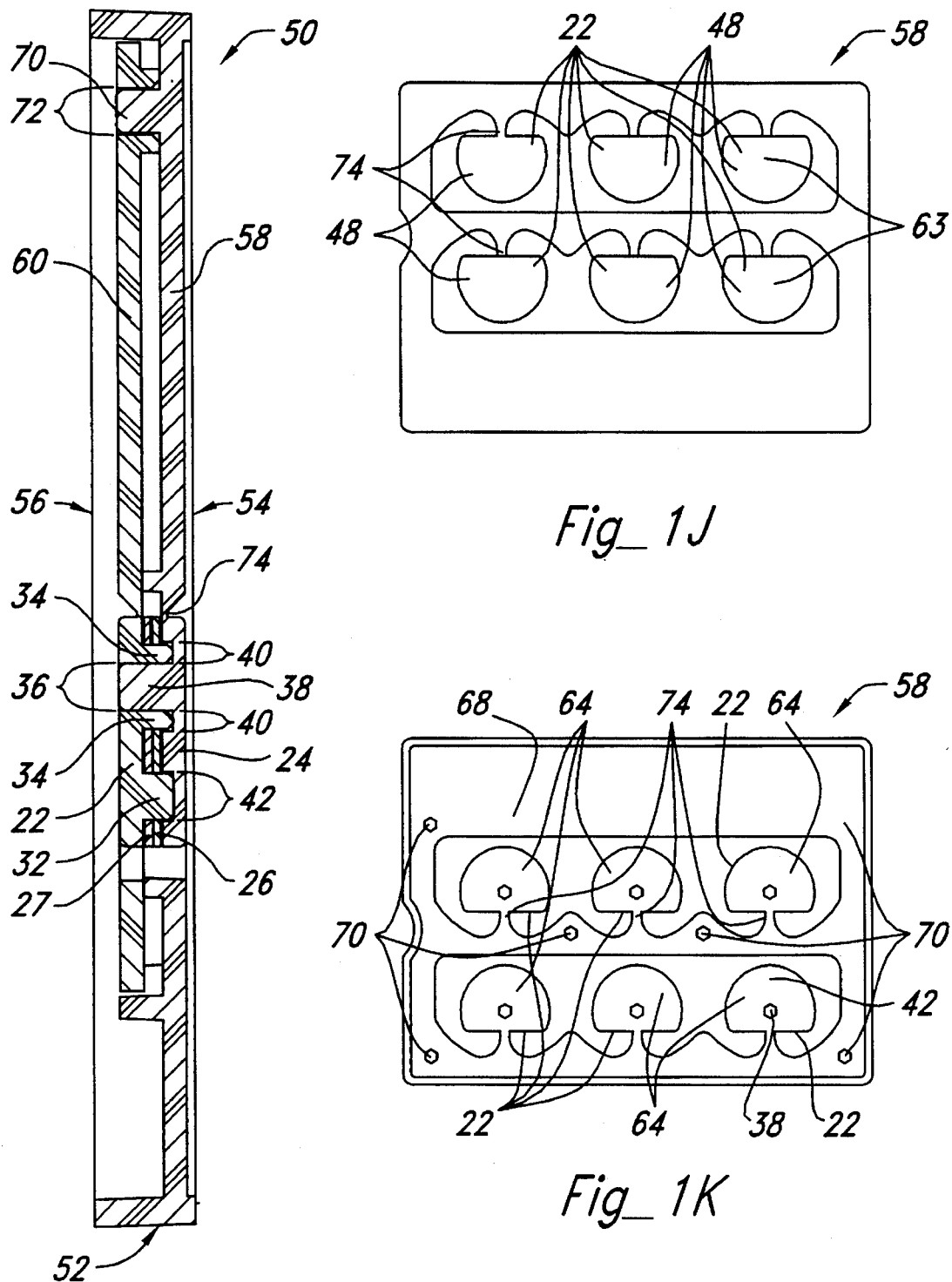

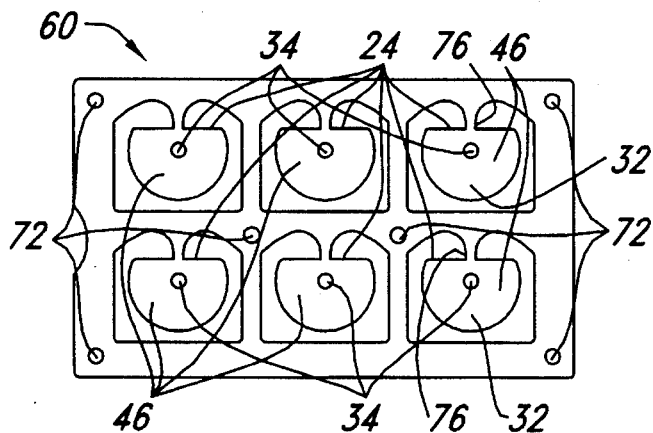
Fig_1L
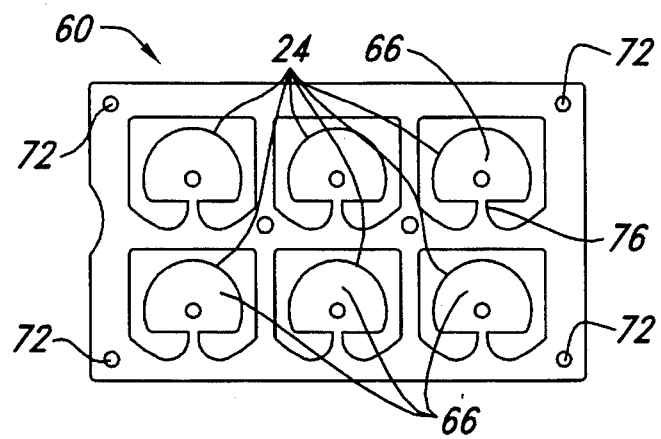
Fig_1M
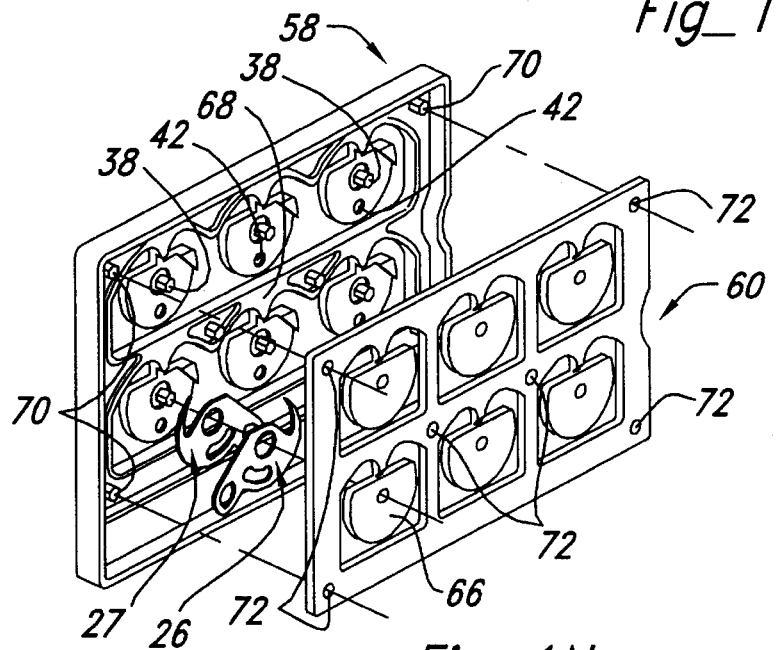
Fig_1N

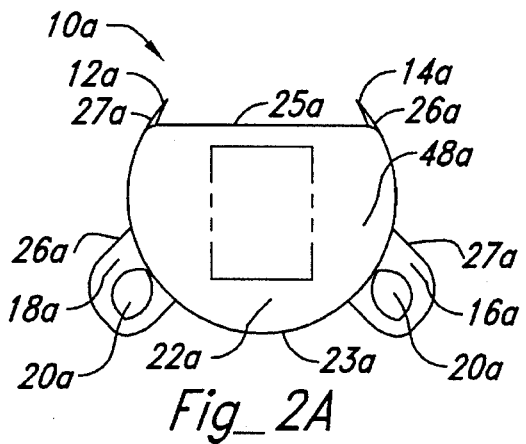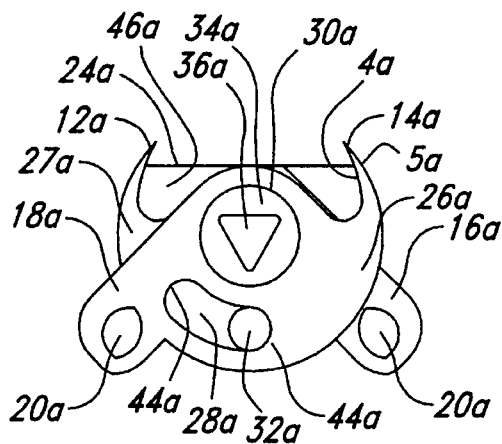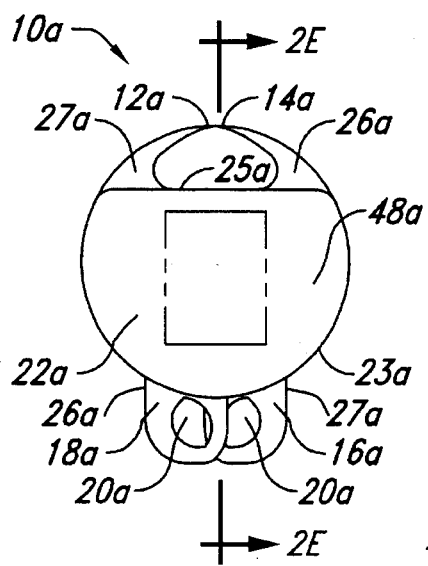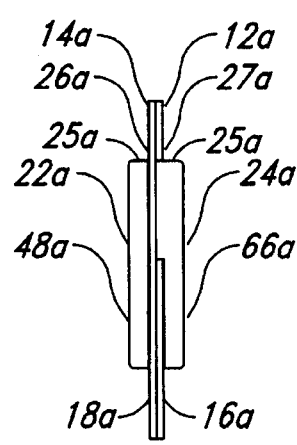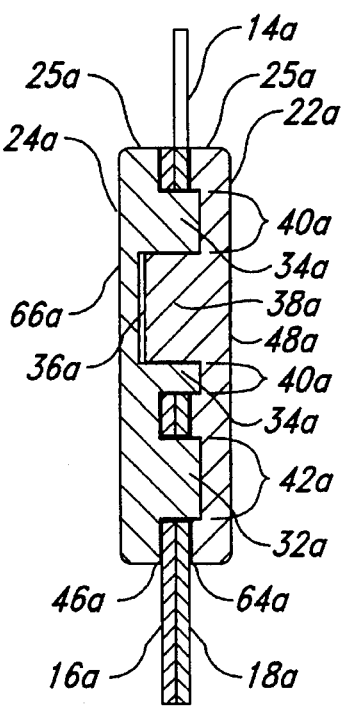

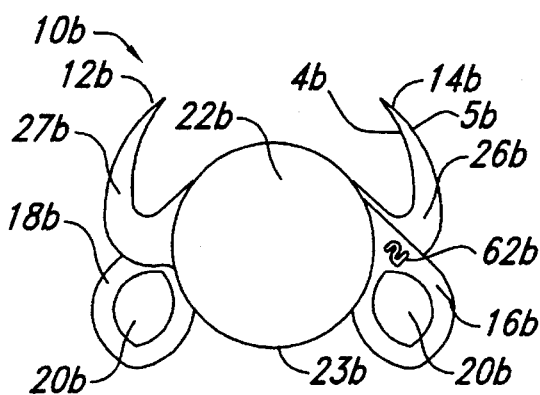
Fig_3A
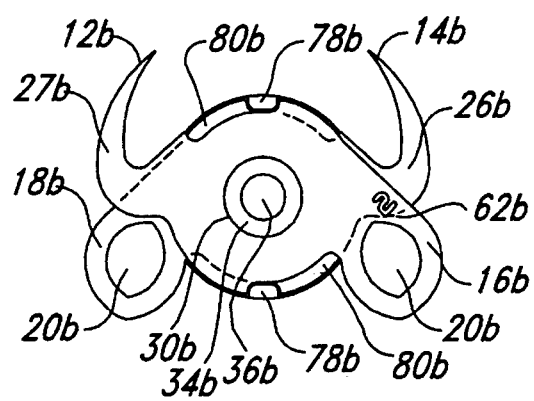
Fig_3C
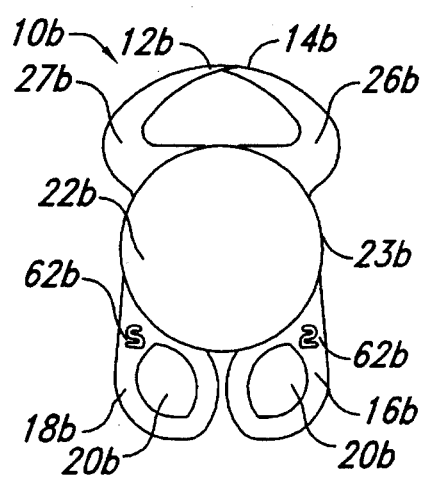
Fig_3B

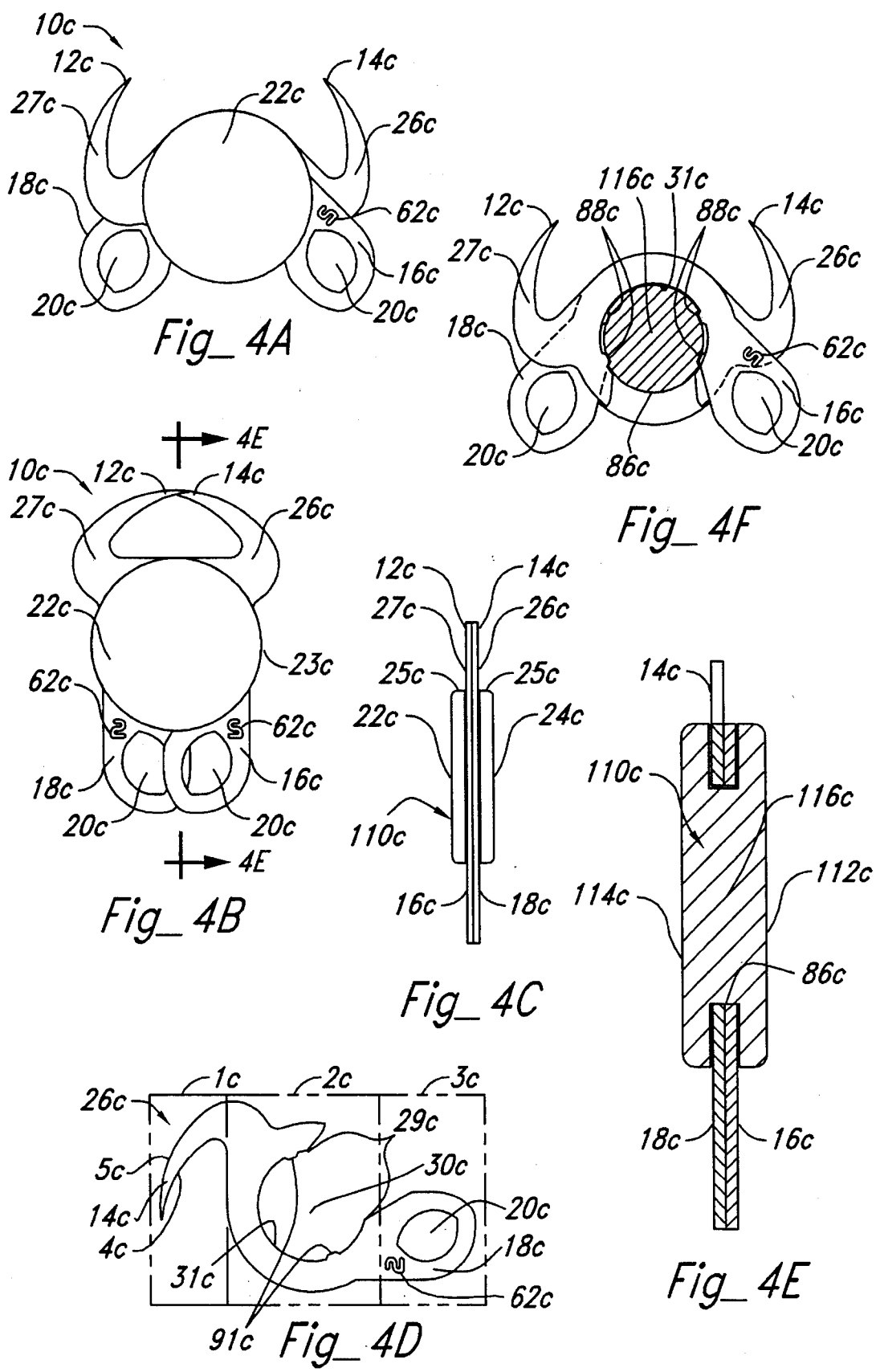

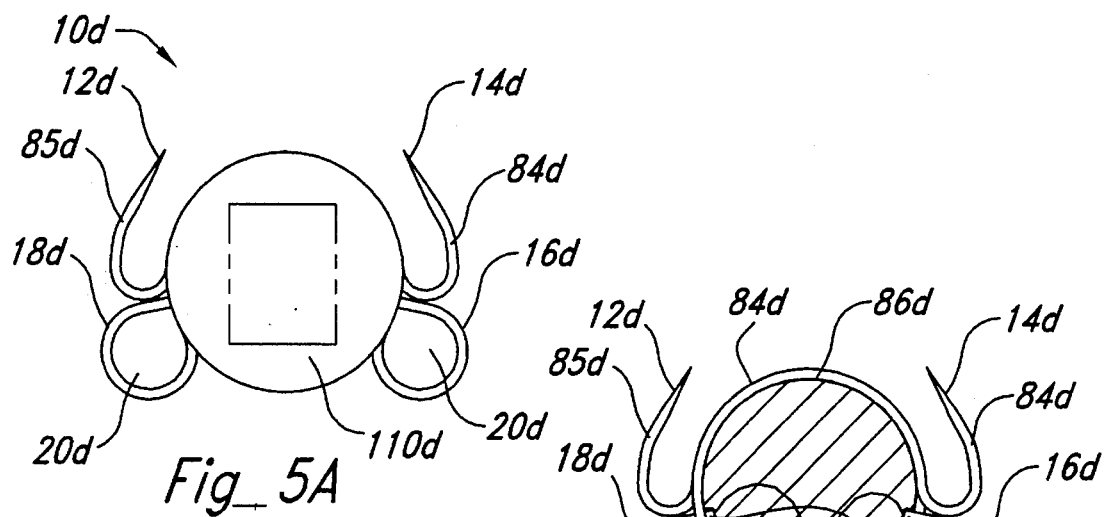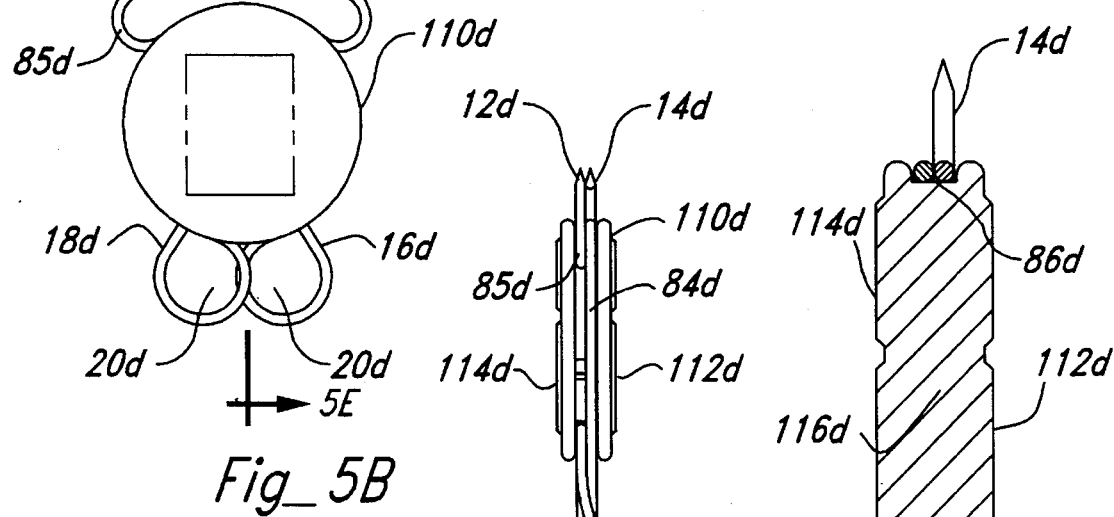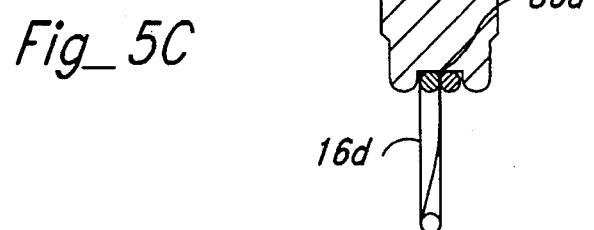

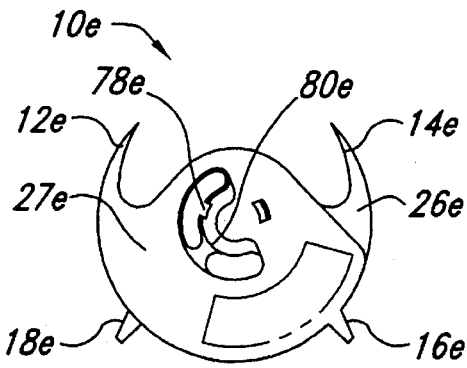
Fig_ 6A
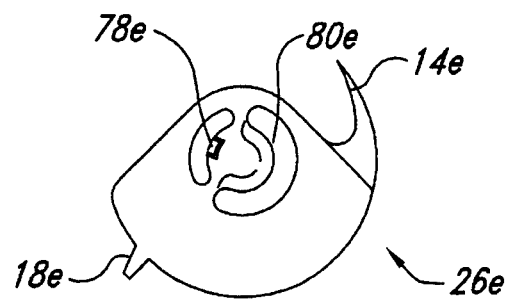
Fig_ 6D
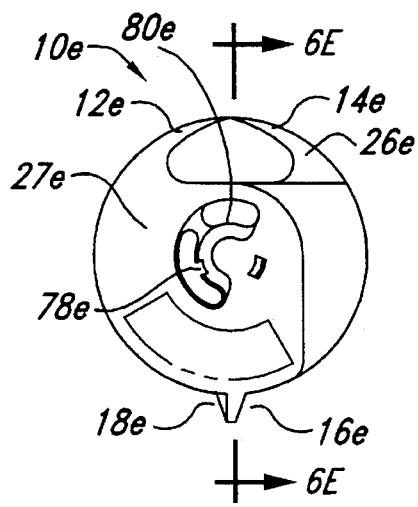
Fig_ 6B
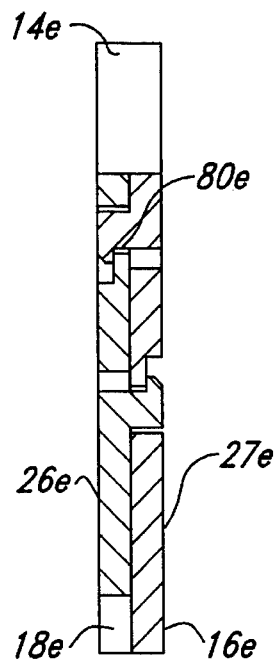
Fig_ 6C
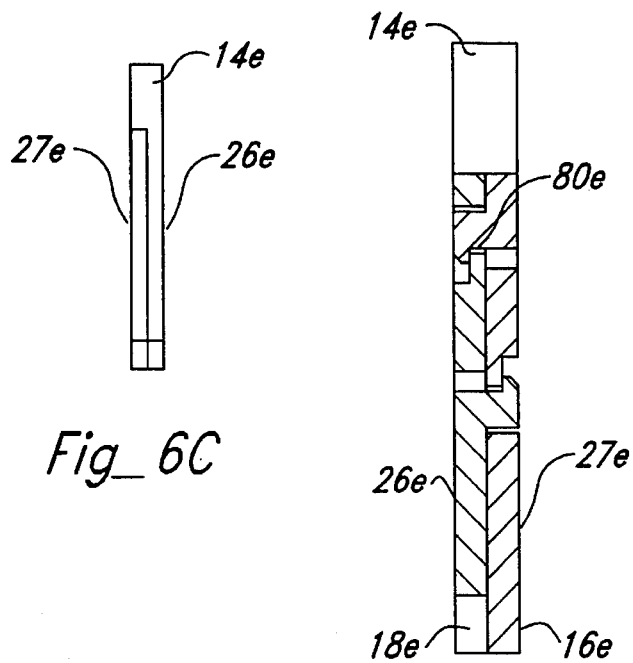
Fig_ 6E

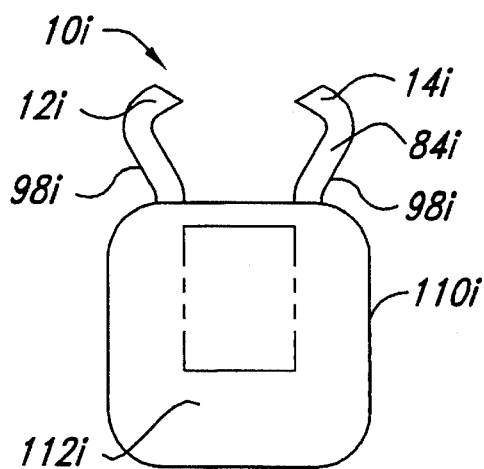
Fig_8A
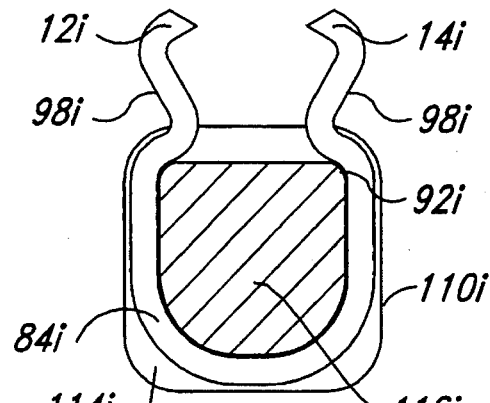
Fig_8D
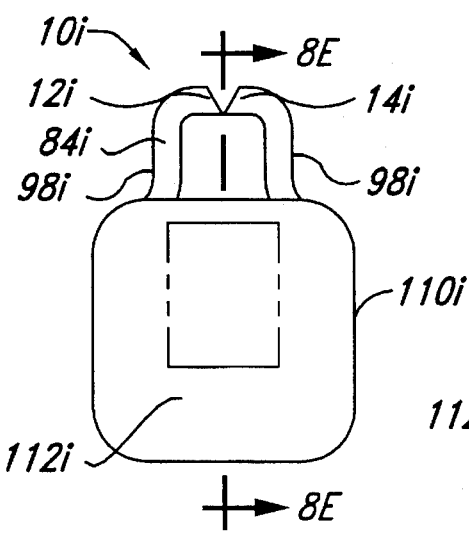
Fig_8B
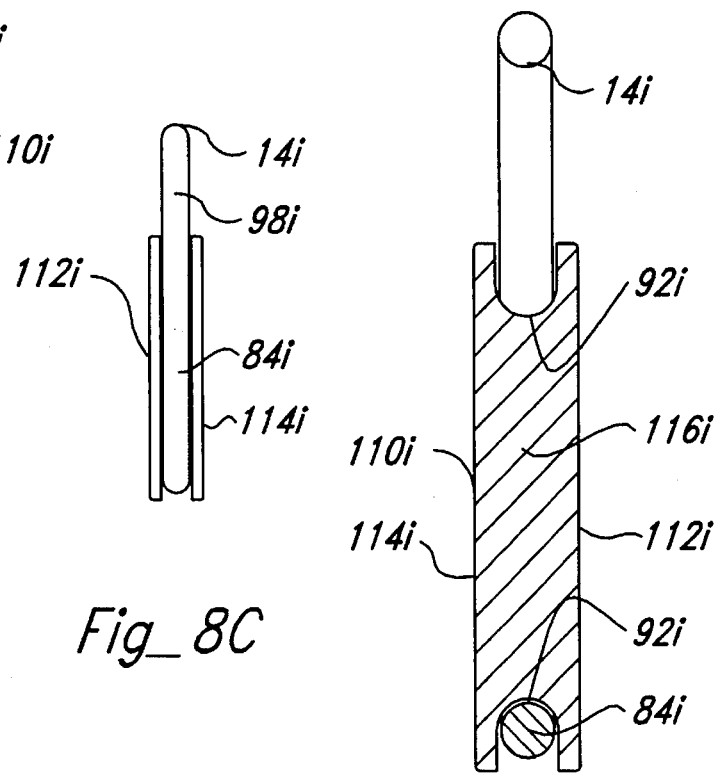
Fig_8C
Fig_8E

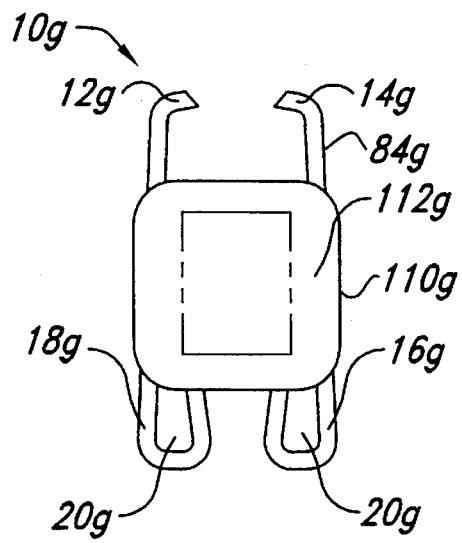
Fig_9A
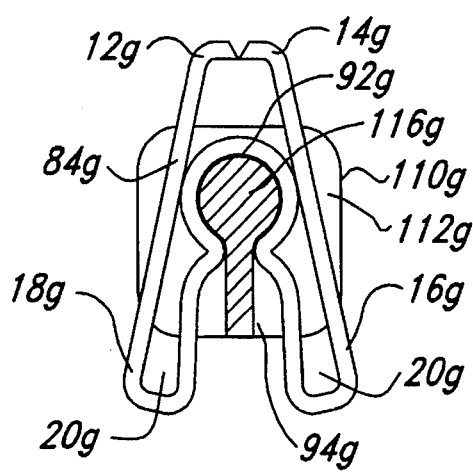
Fig_9D
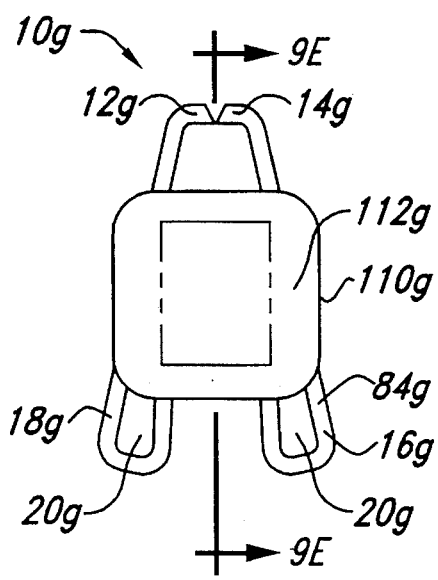
Fig_9B
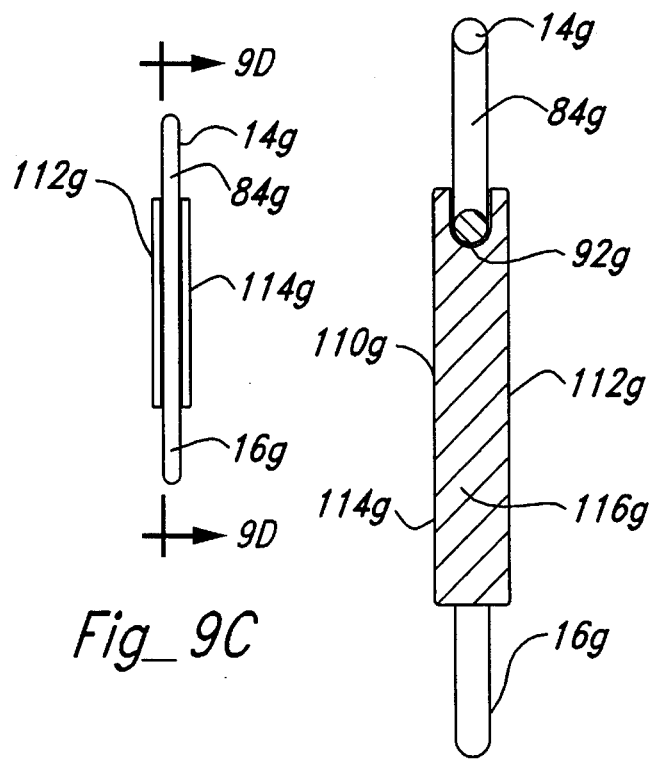
Fig_9C
Fig_9E

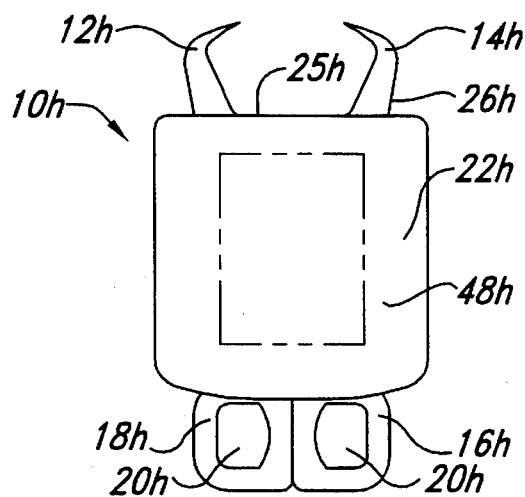
Fig_ 10A
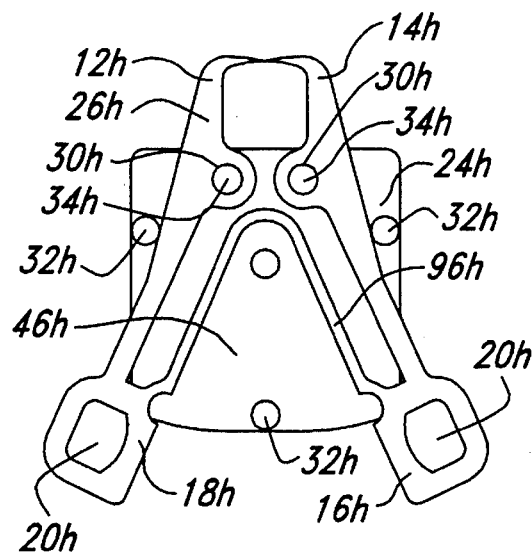
Fig_ 10D
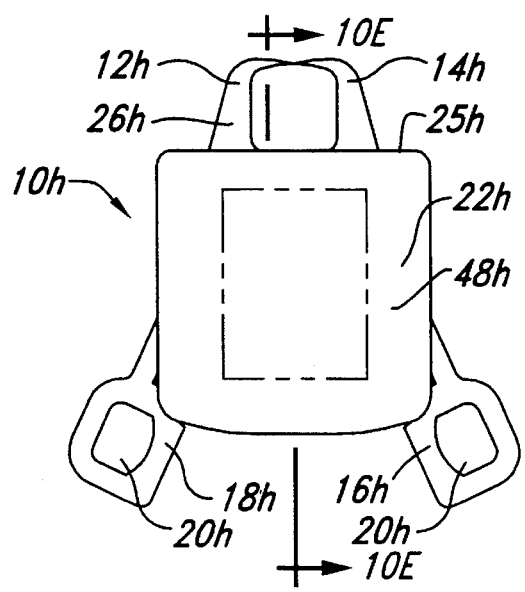
Fig_ 10B
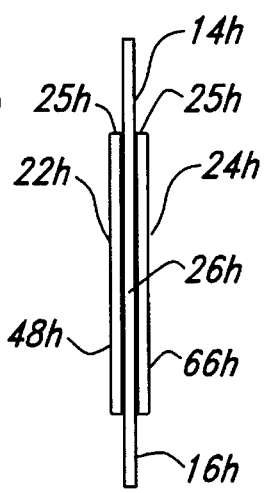
Fig_ 10C
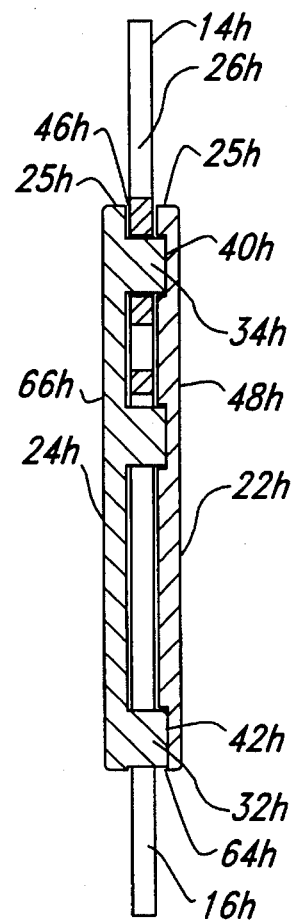
Fig_ 10E

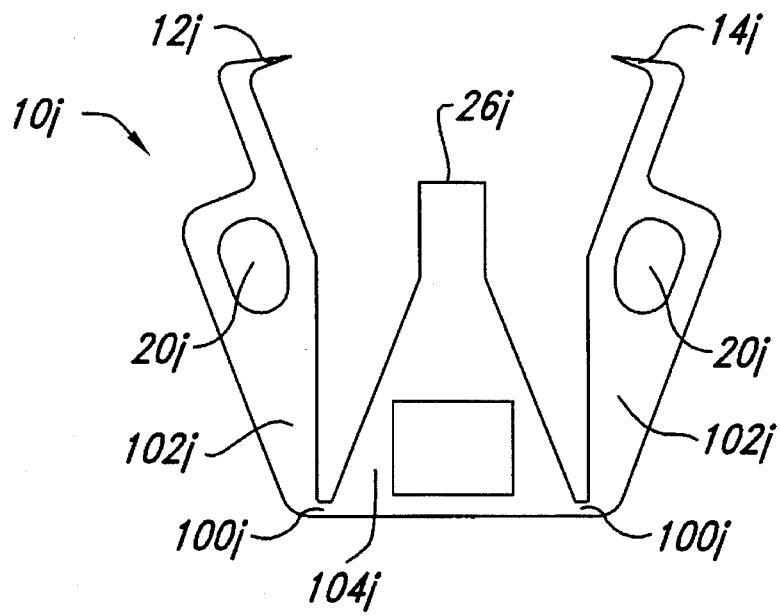
Fig_11A
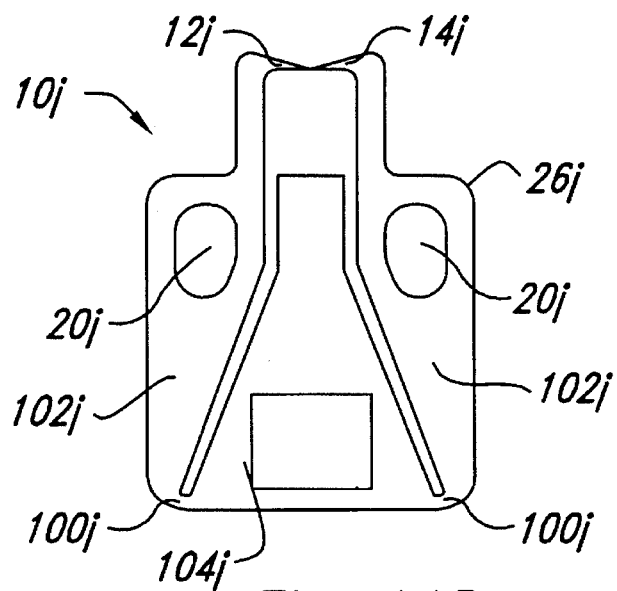
Fig_11B
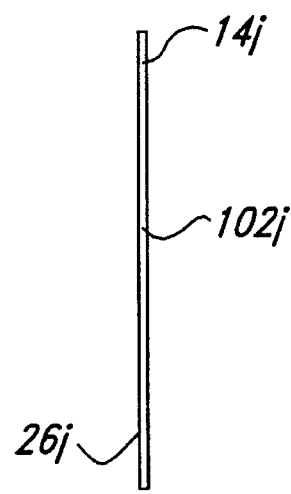
Fig_11C

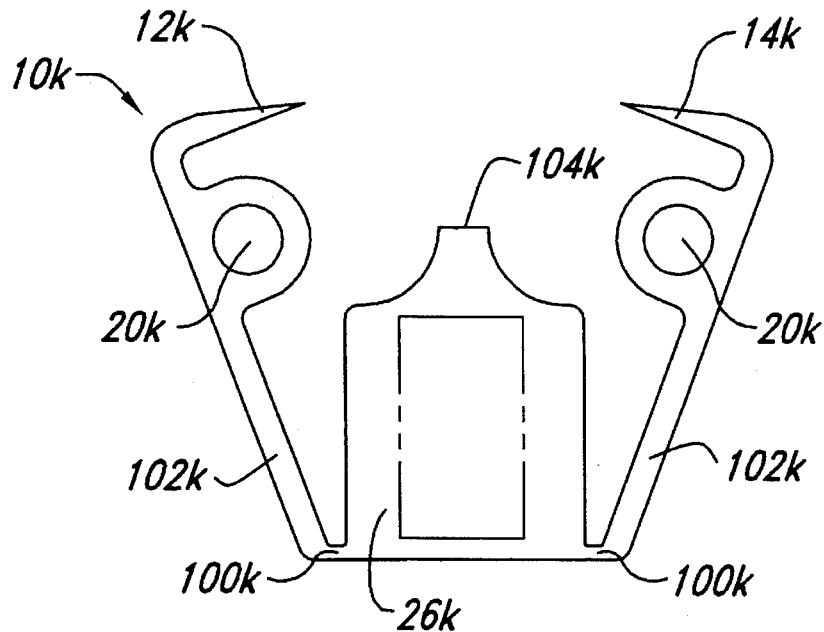
Fig_12A
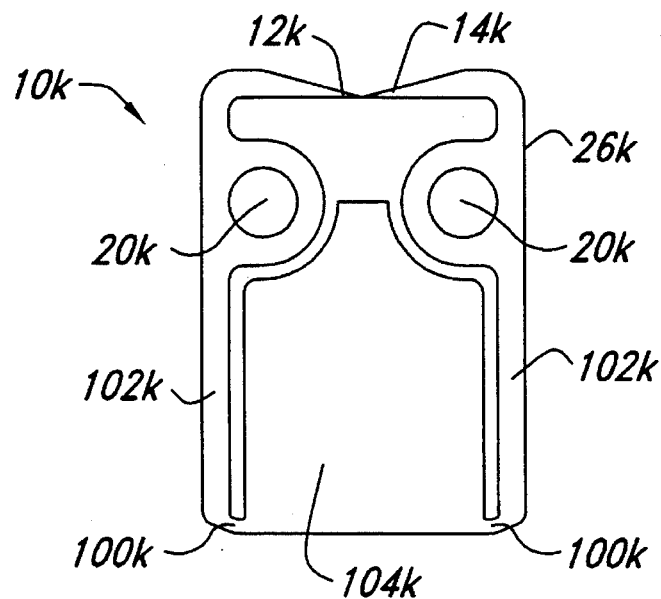
Fig_12B
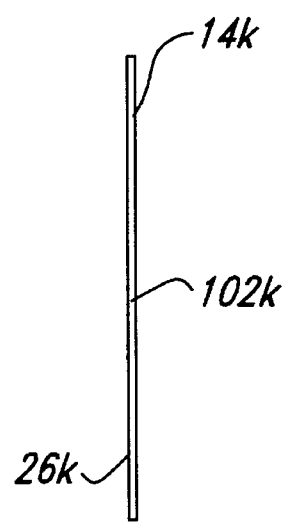
Fig_12C

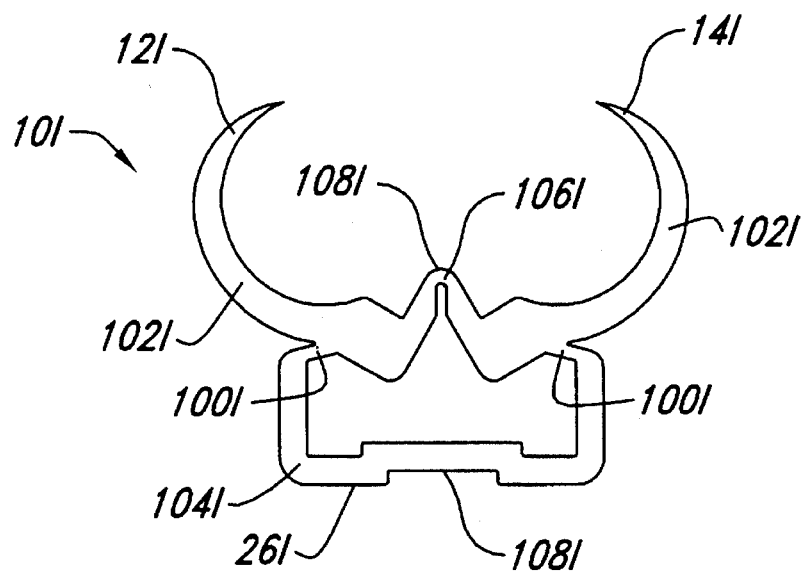
Fig_ 13A
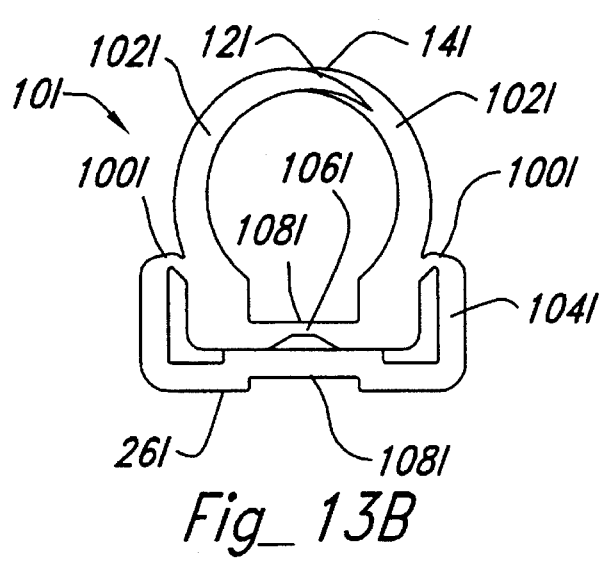
Fig_ 13B
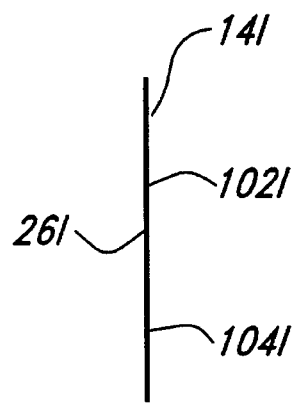
Fig_ 13C

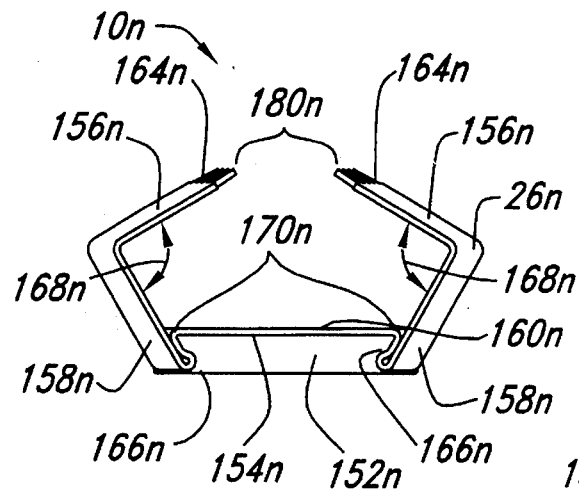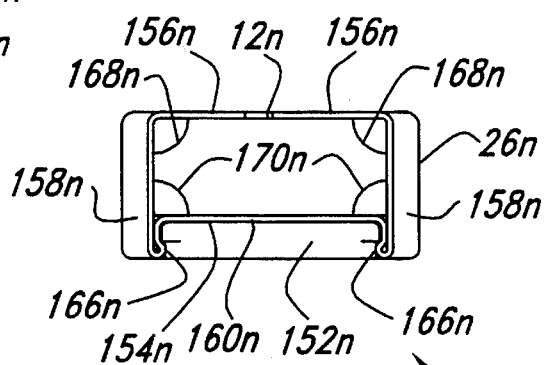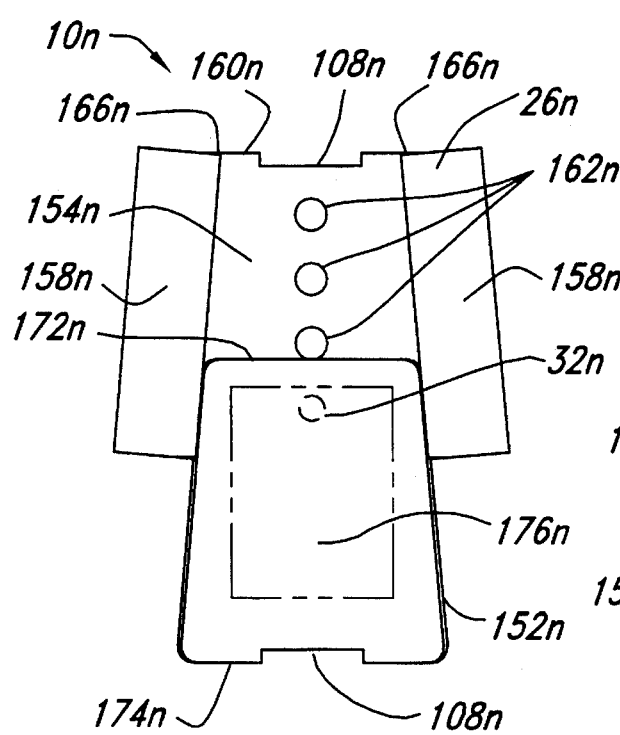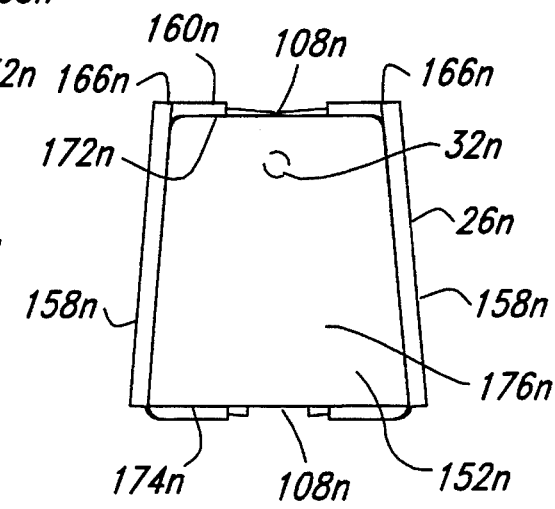

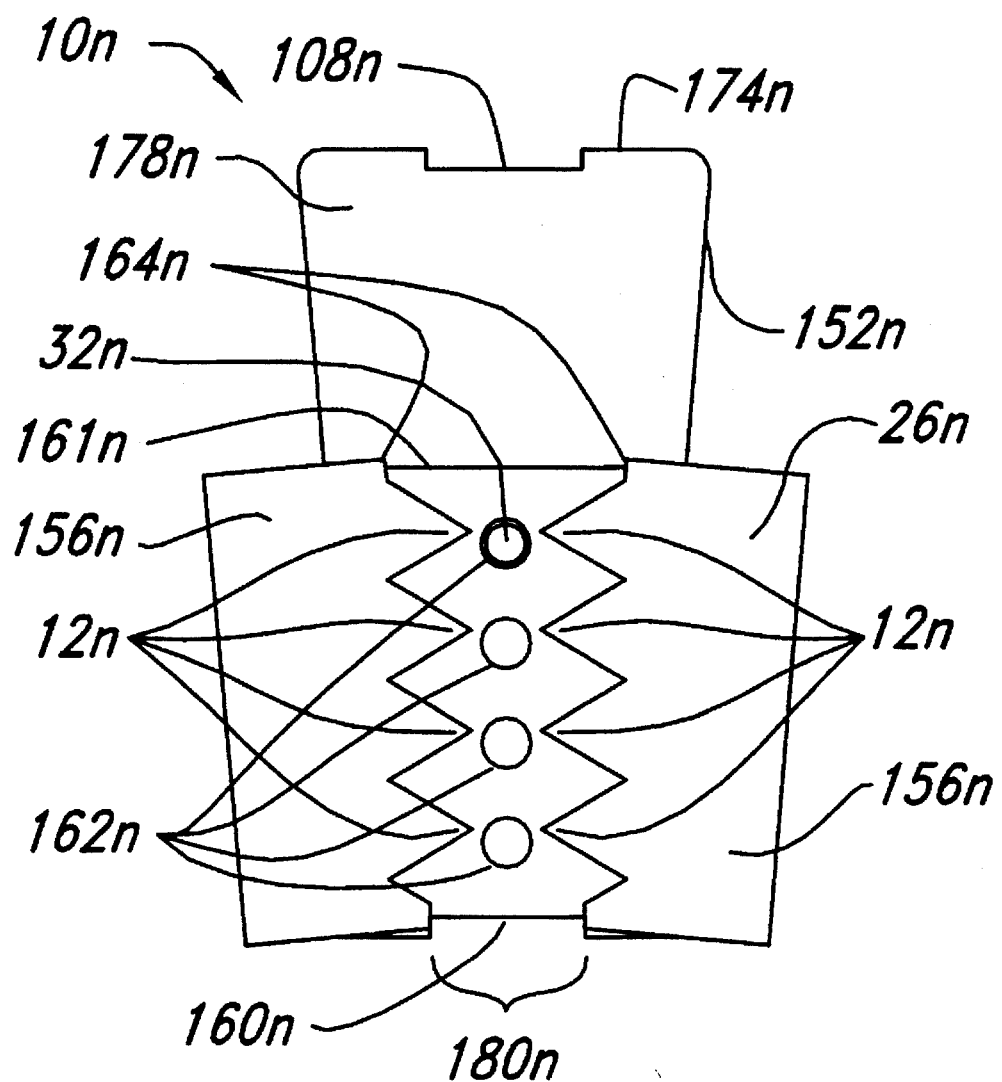
Fig_ 15E

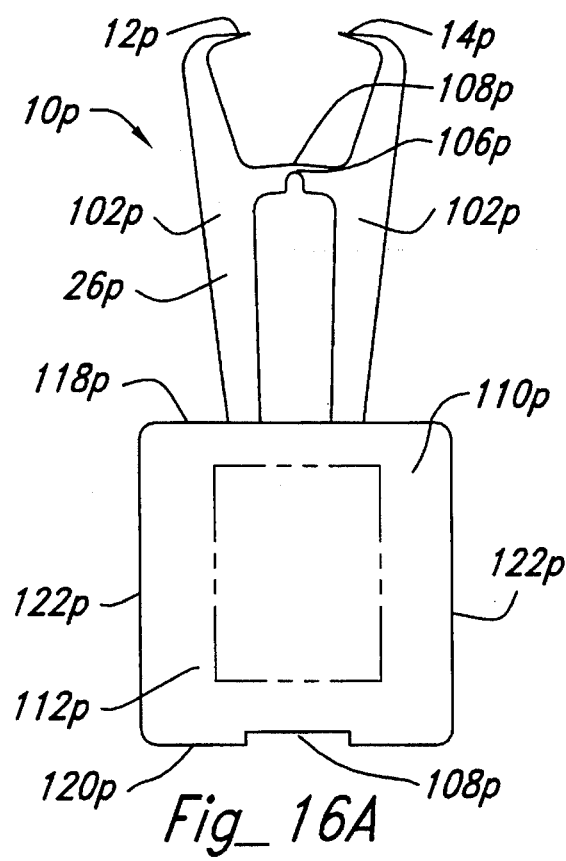
Fig_ 16A
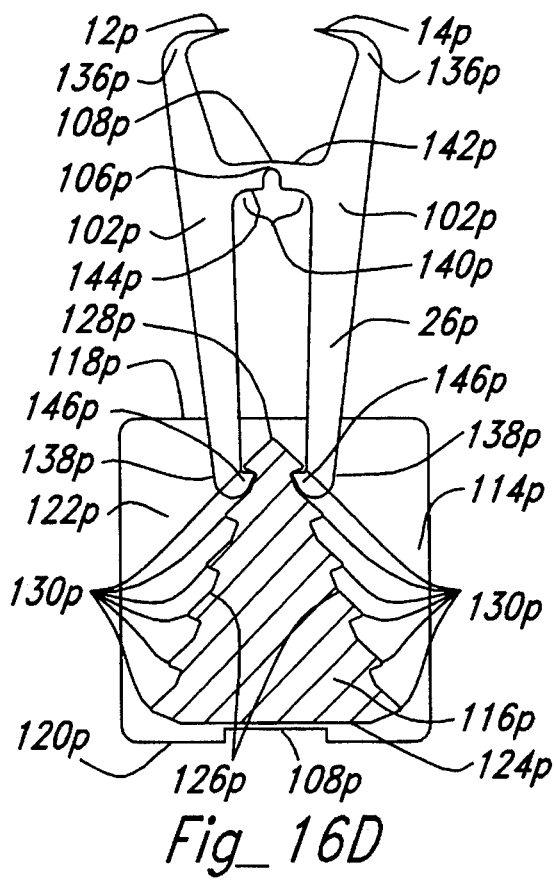
Fig_ 16D
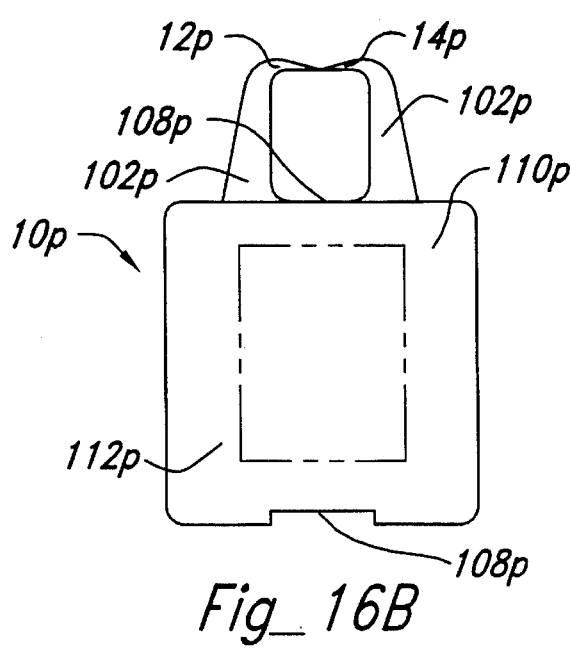
Fig_ 16B
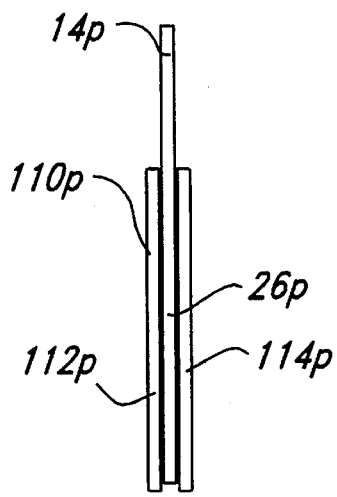
Fig_ 16C

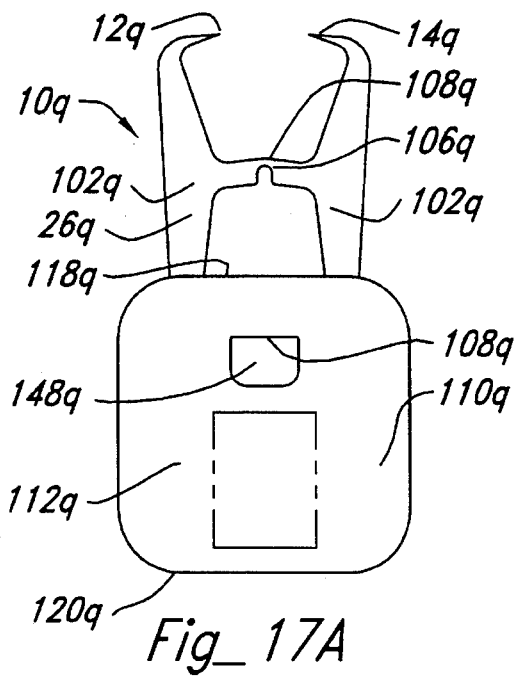
Fig_ 17A
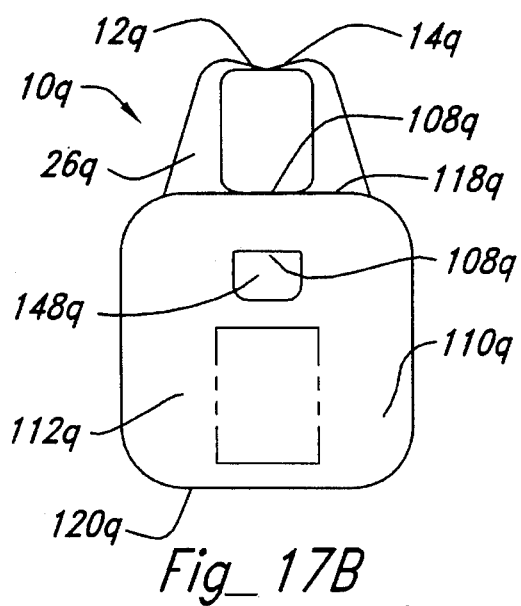
Fig_ 17B
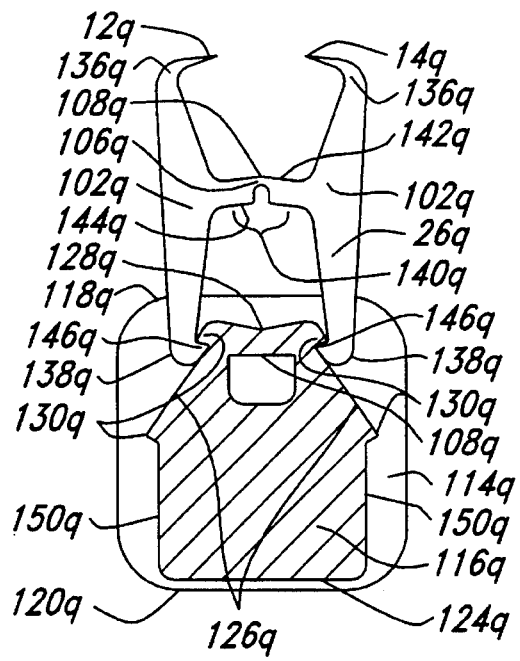
Fig_ 17D
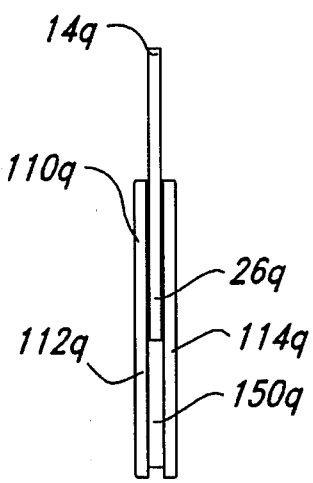
Fig_ 17C

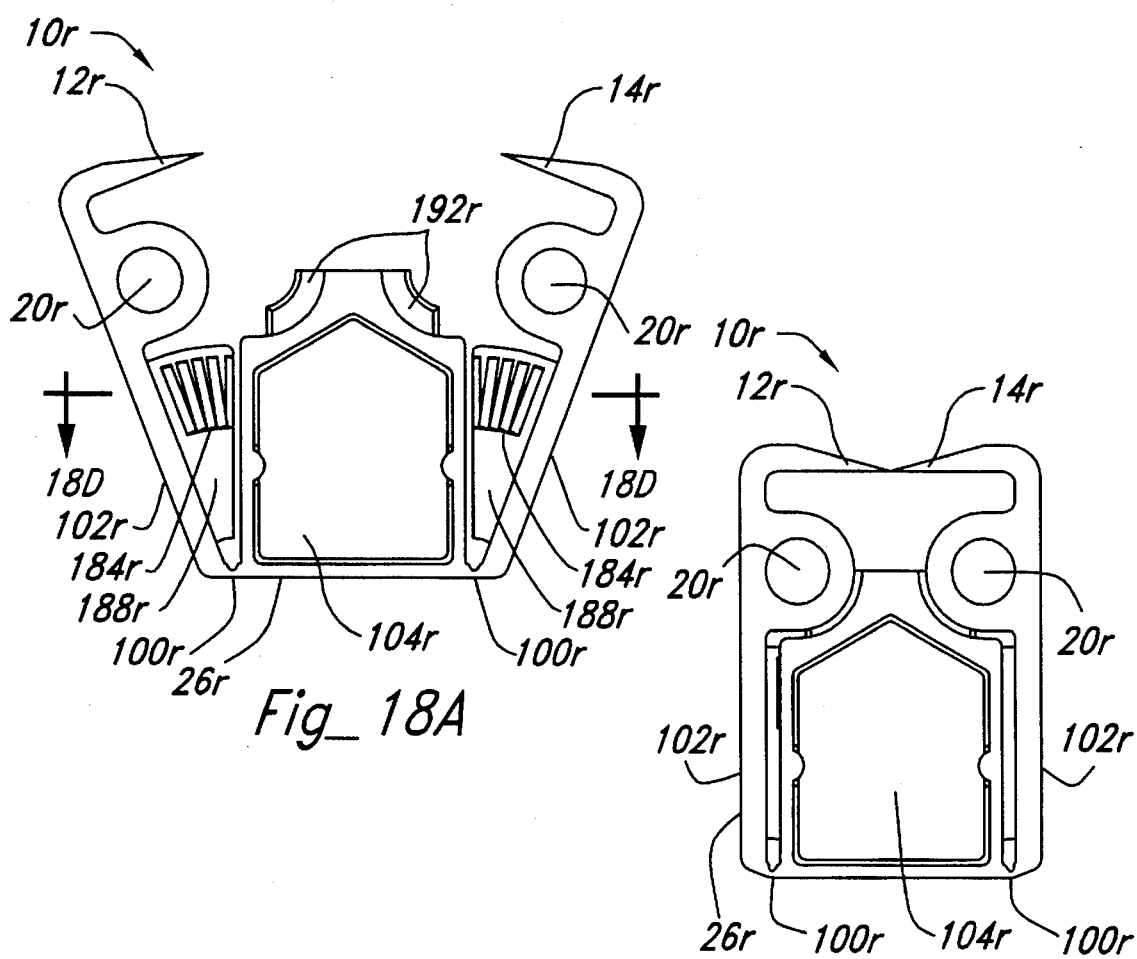

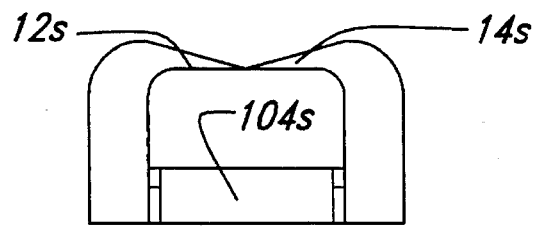
Fig_19E
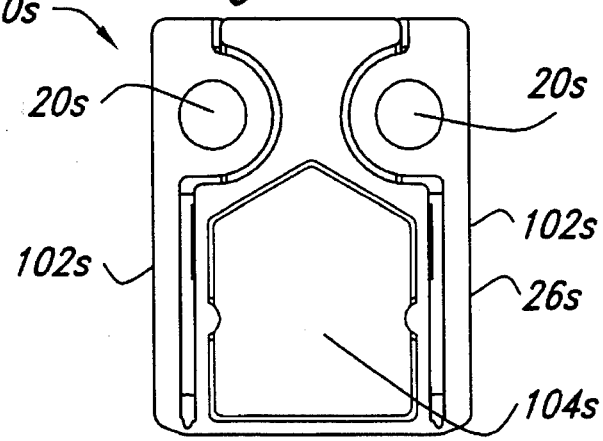
Fig_19B
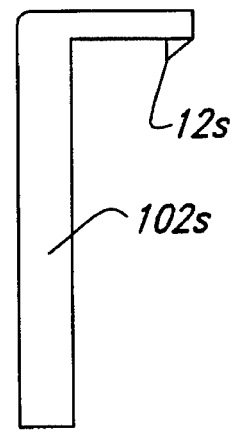
Fig_19C
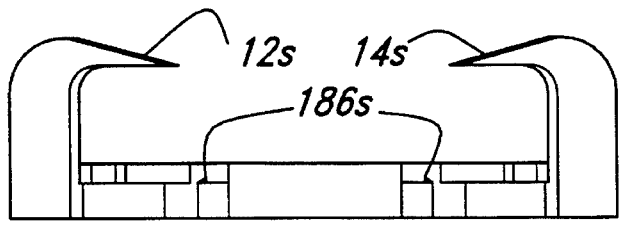
Fig_19D
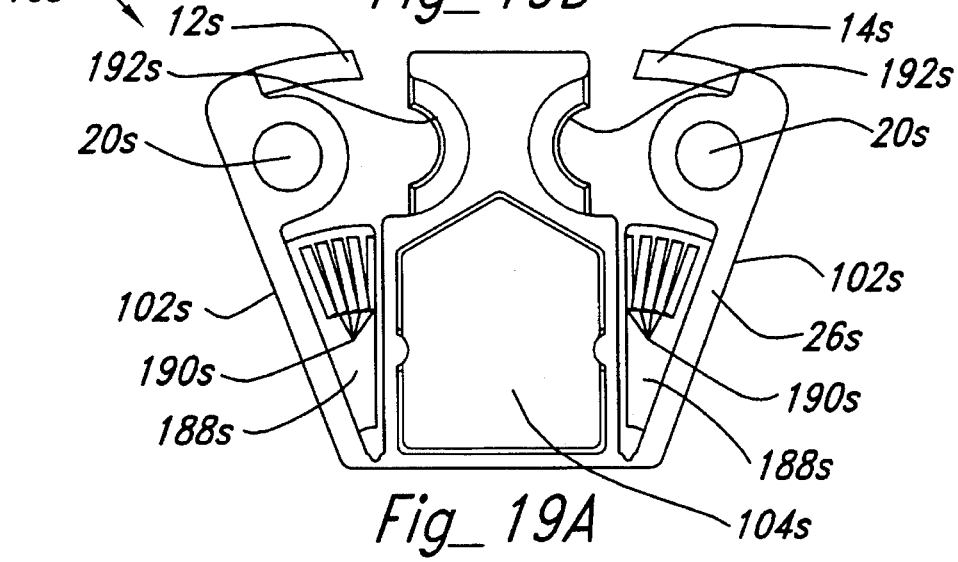
Fig_19A

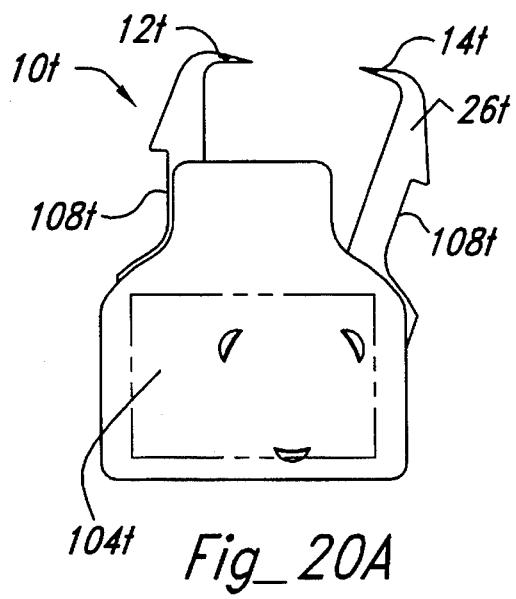
Fig_20A
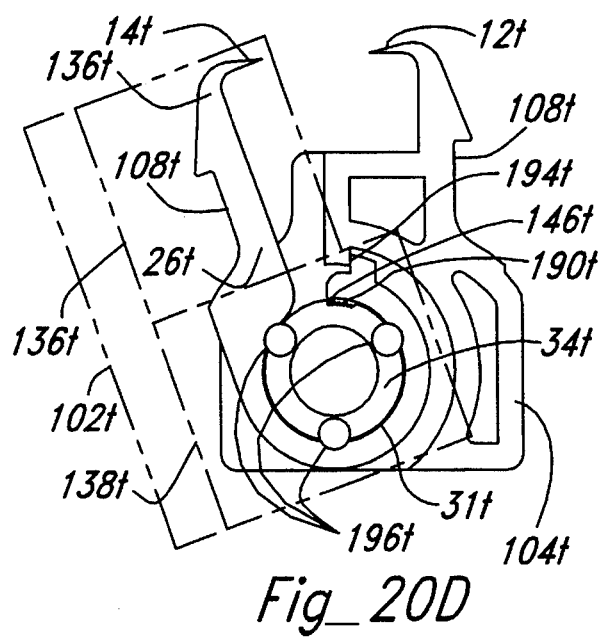
Fig_20D
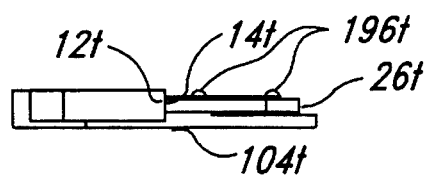
Fig_20C
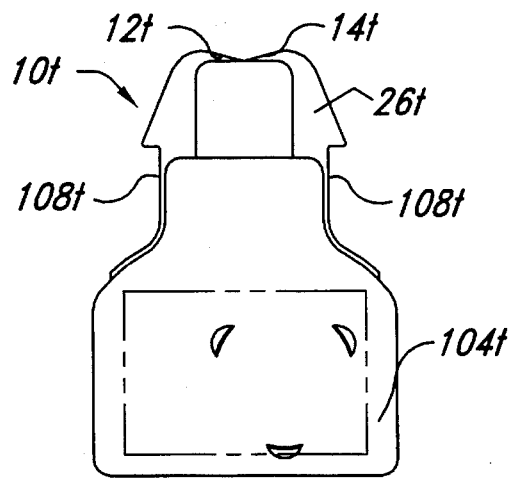
Fig_20B

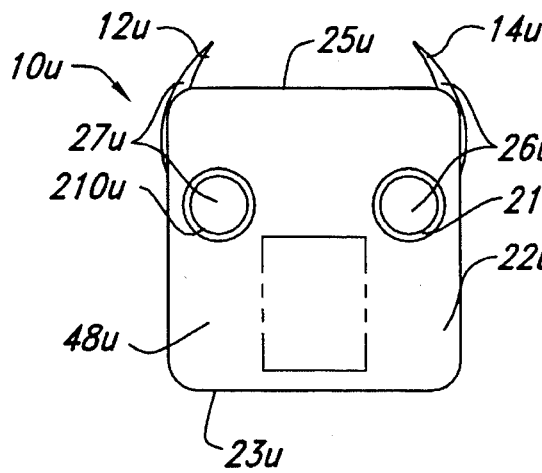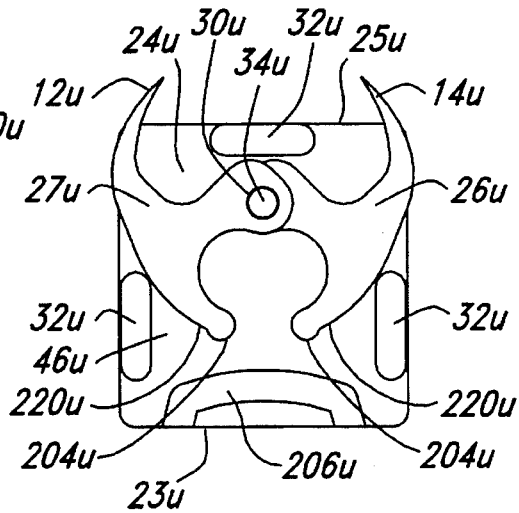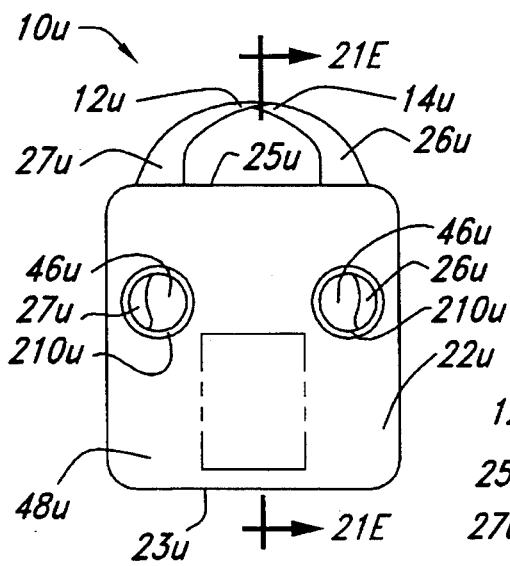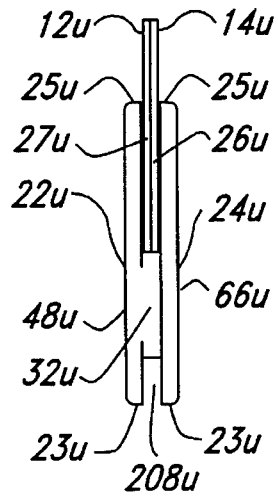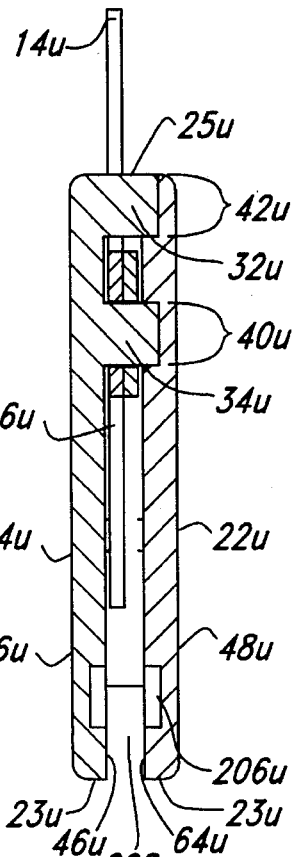
Fig_21A
Fig_21B
Fig_21C
Fig_21D
Fig_21E

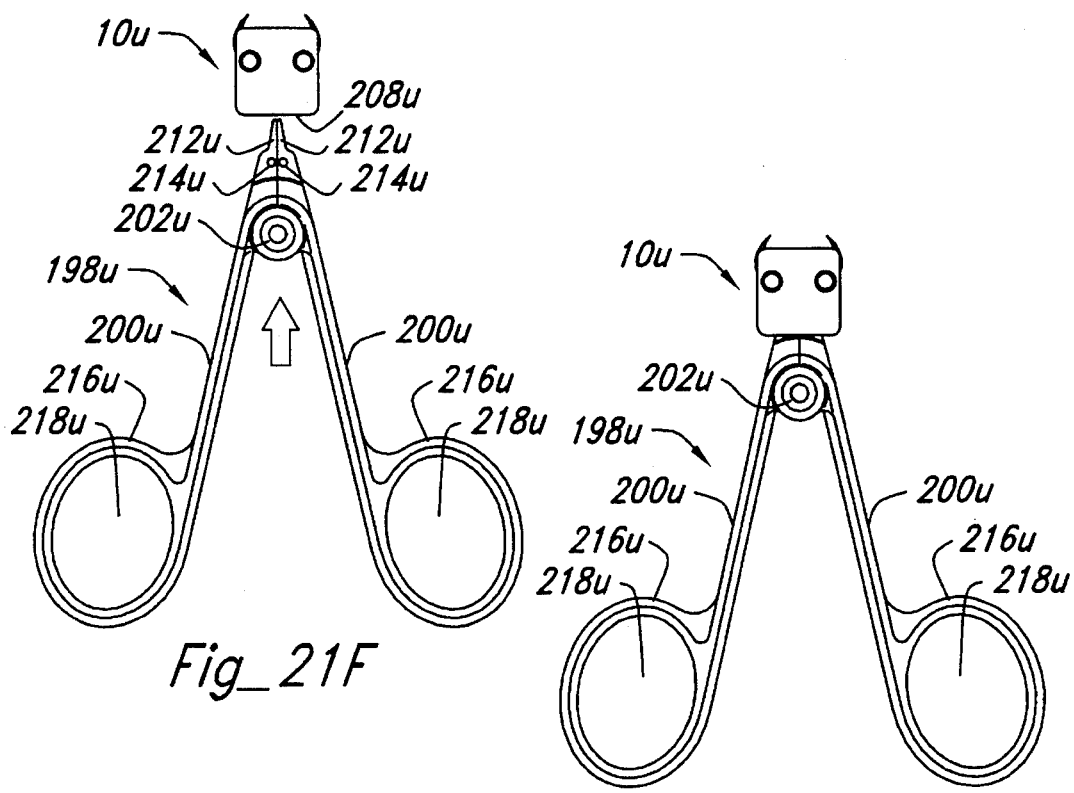
Fig_21F
Fig_21G
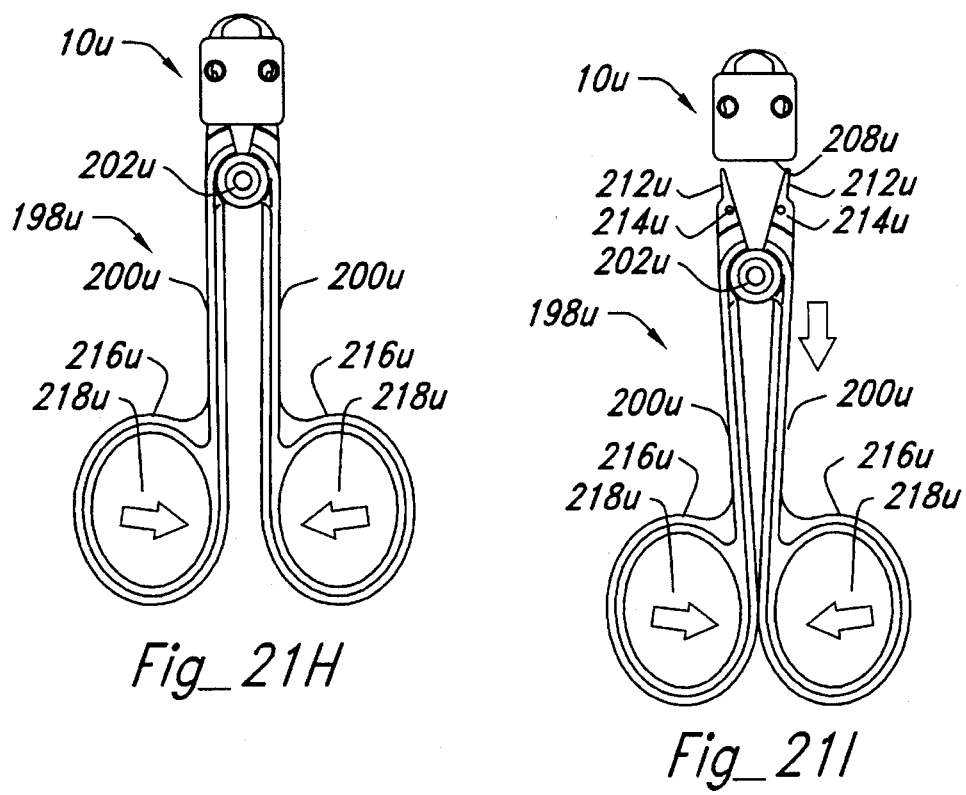
Fig_21H
Fig_21I

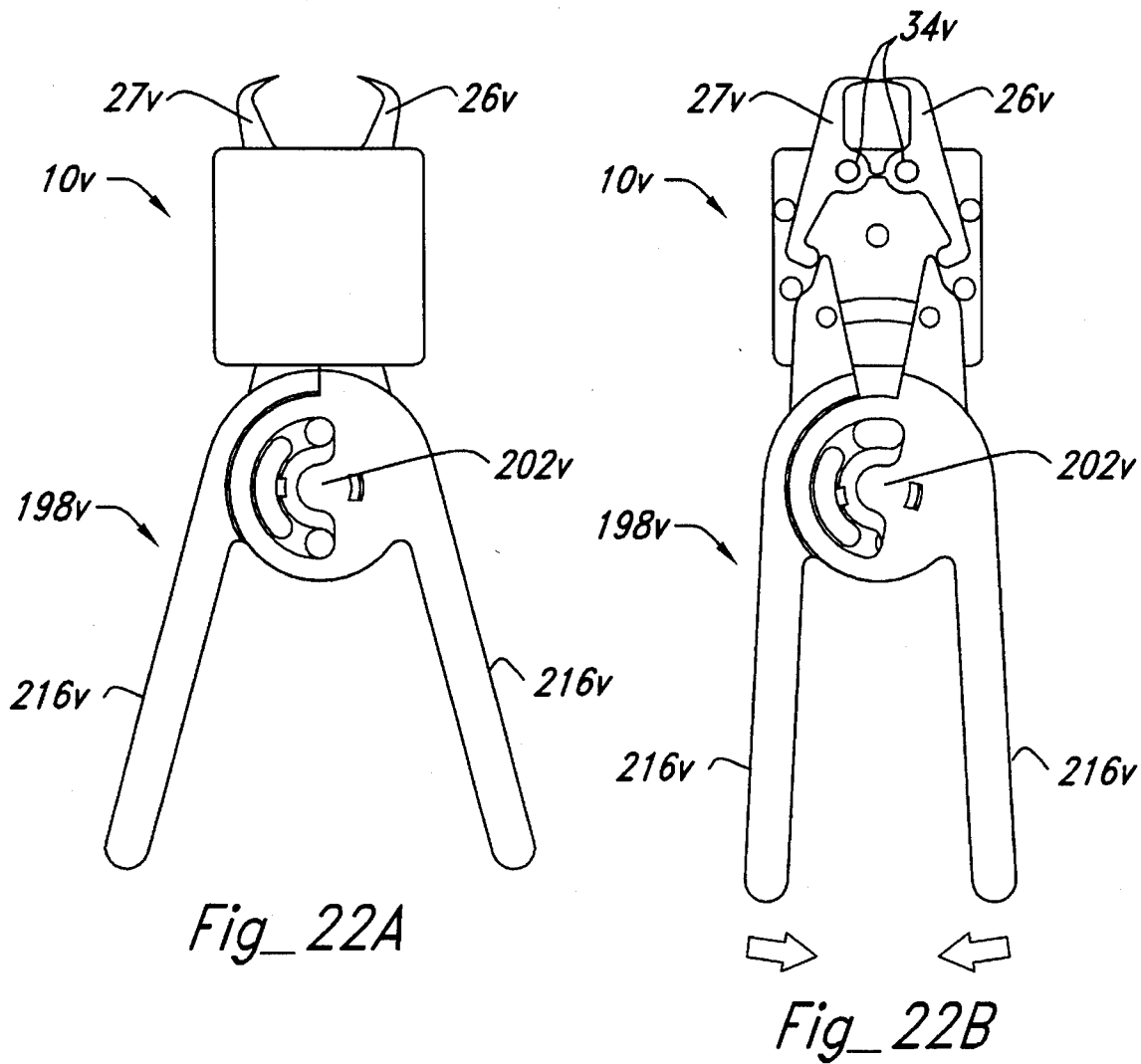
Fig_22A
Fig_22B

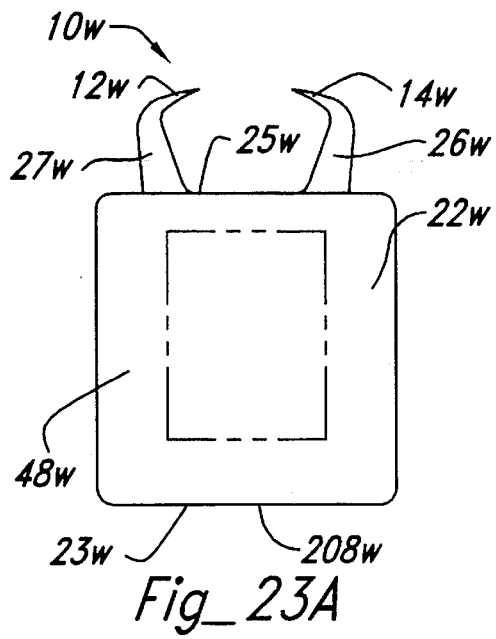
Fig_23A
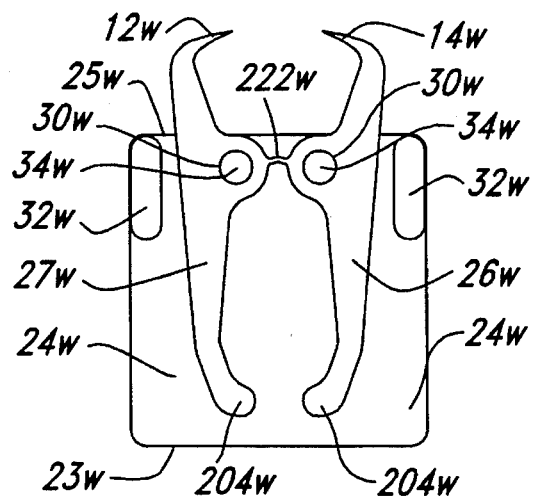
Fig_23D
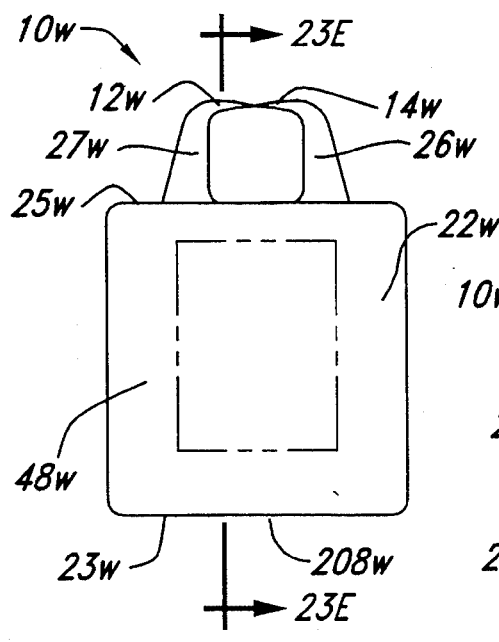
Fig_23B
Fig_23C
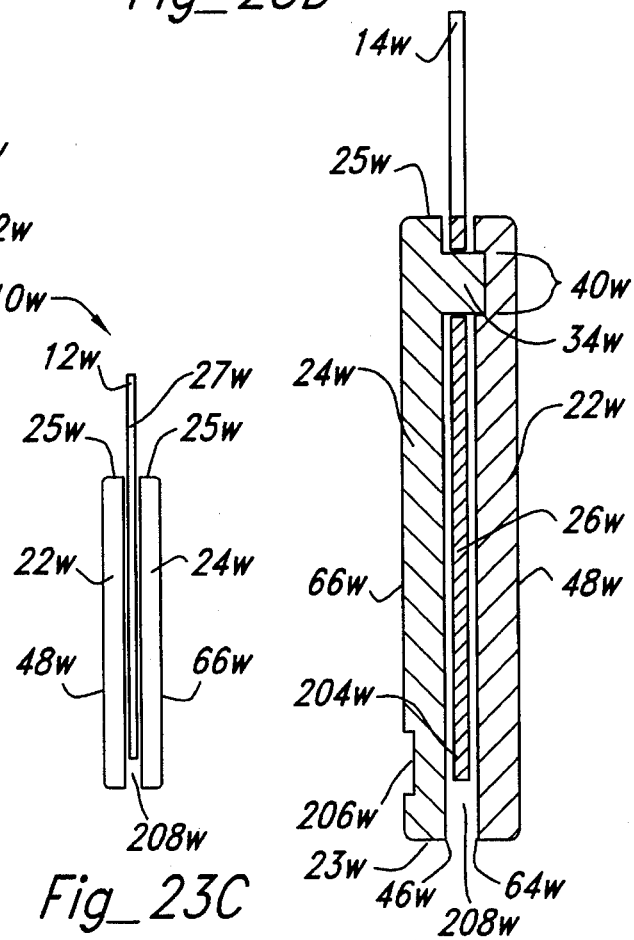
Fig_23E

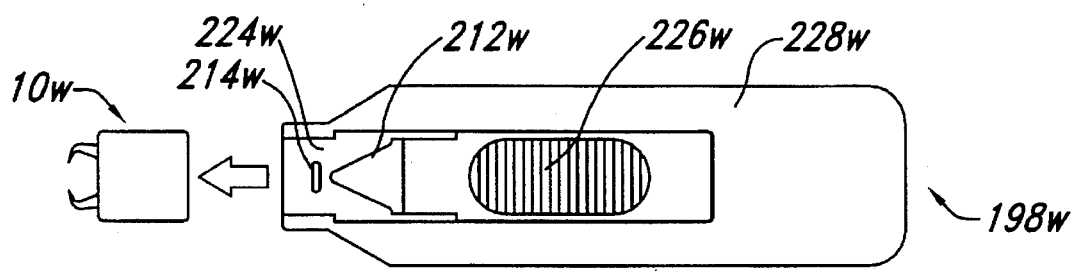
Fig_23F
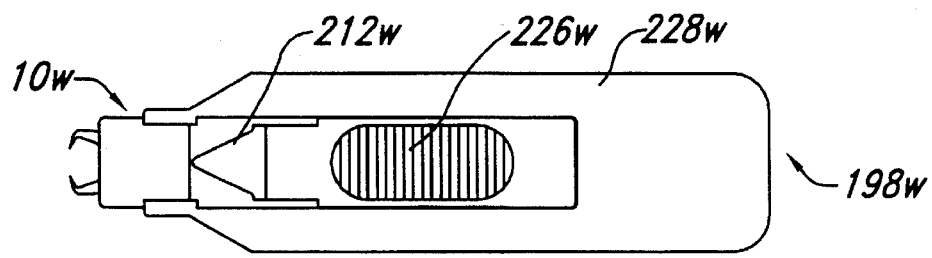
Fig_23G
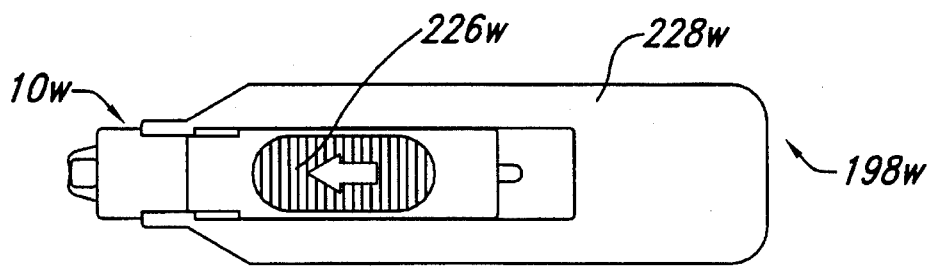
Fig_23H
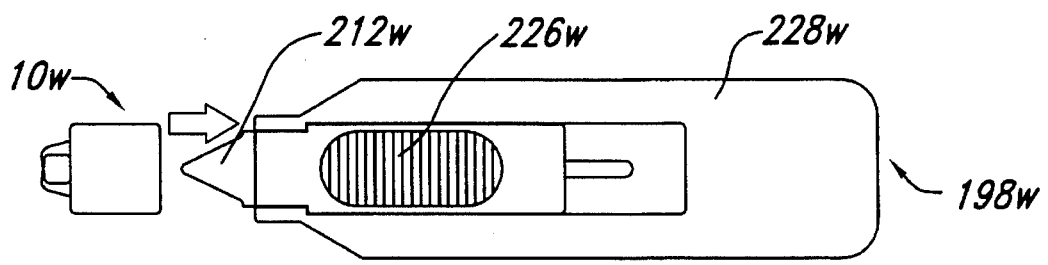
Fig_23I

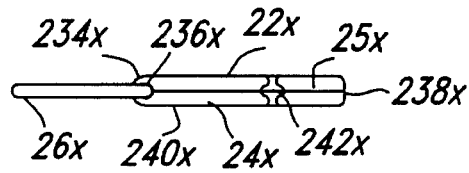
Fig_24C
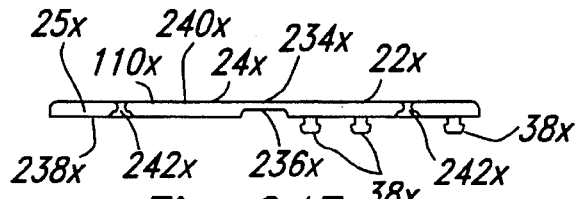
Fig_24F
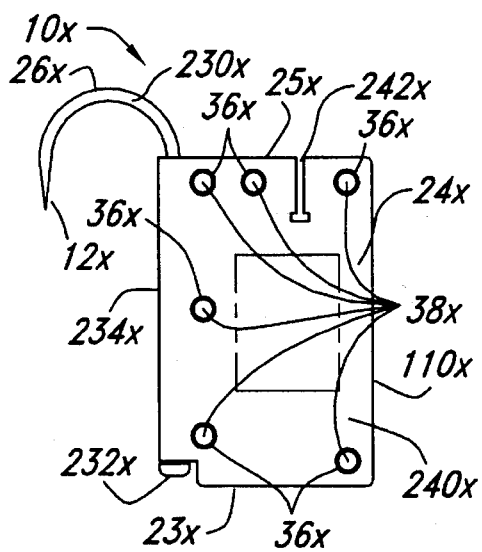
Fig_24A
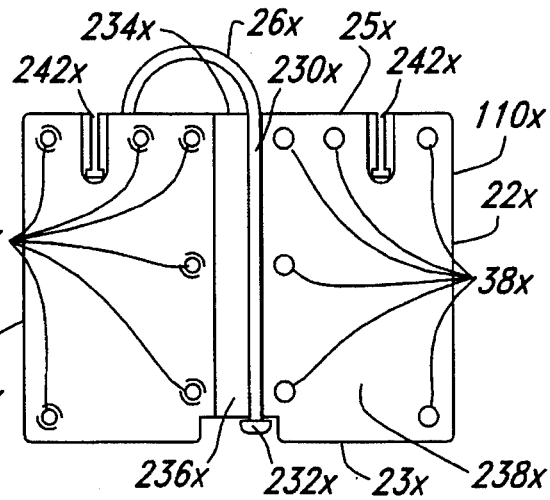
Fig_24D
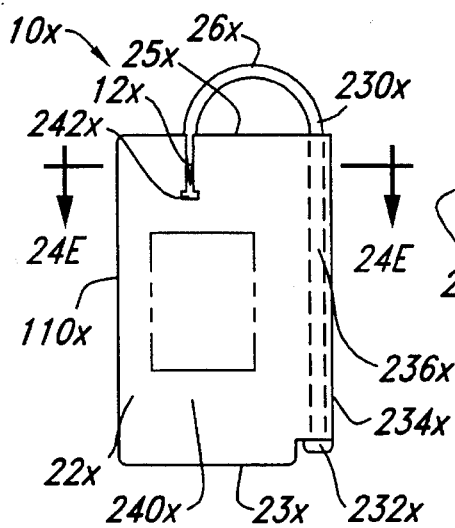
Fig_24B
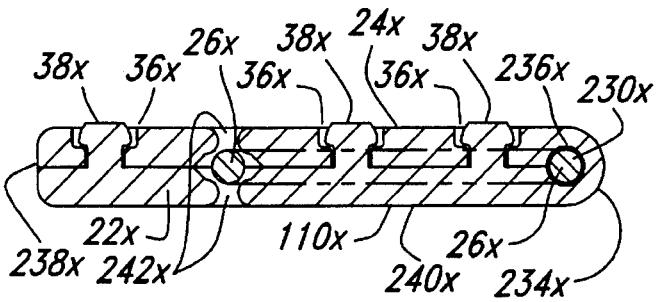
Fig_24E

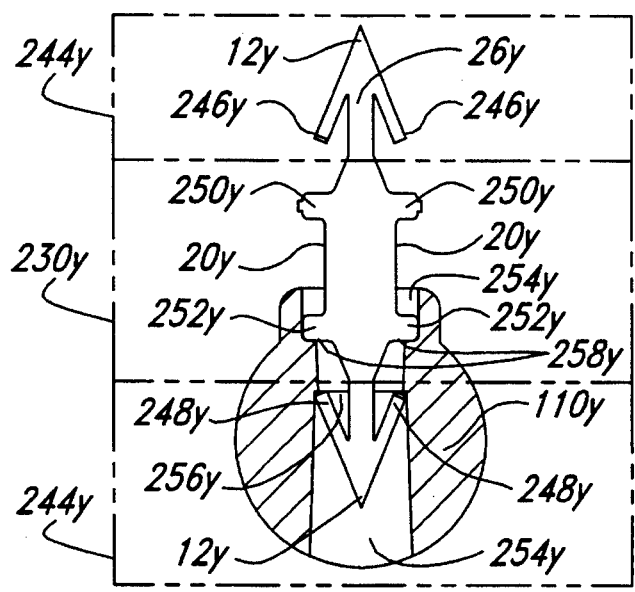
Fig_25C
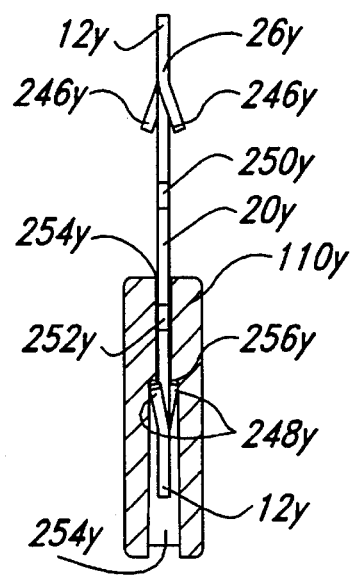
Fig_25D
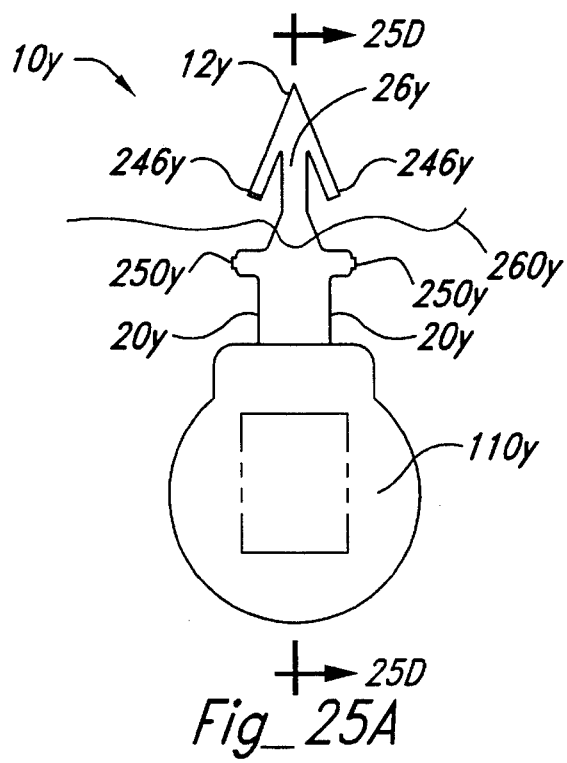
Fig_25A
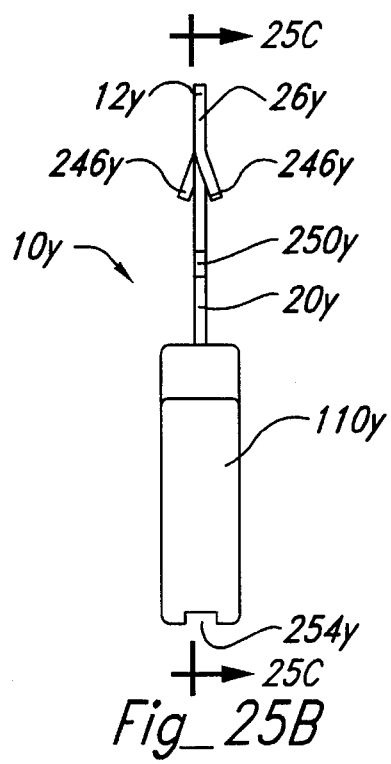
Fig_25B

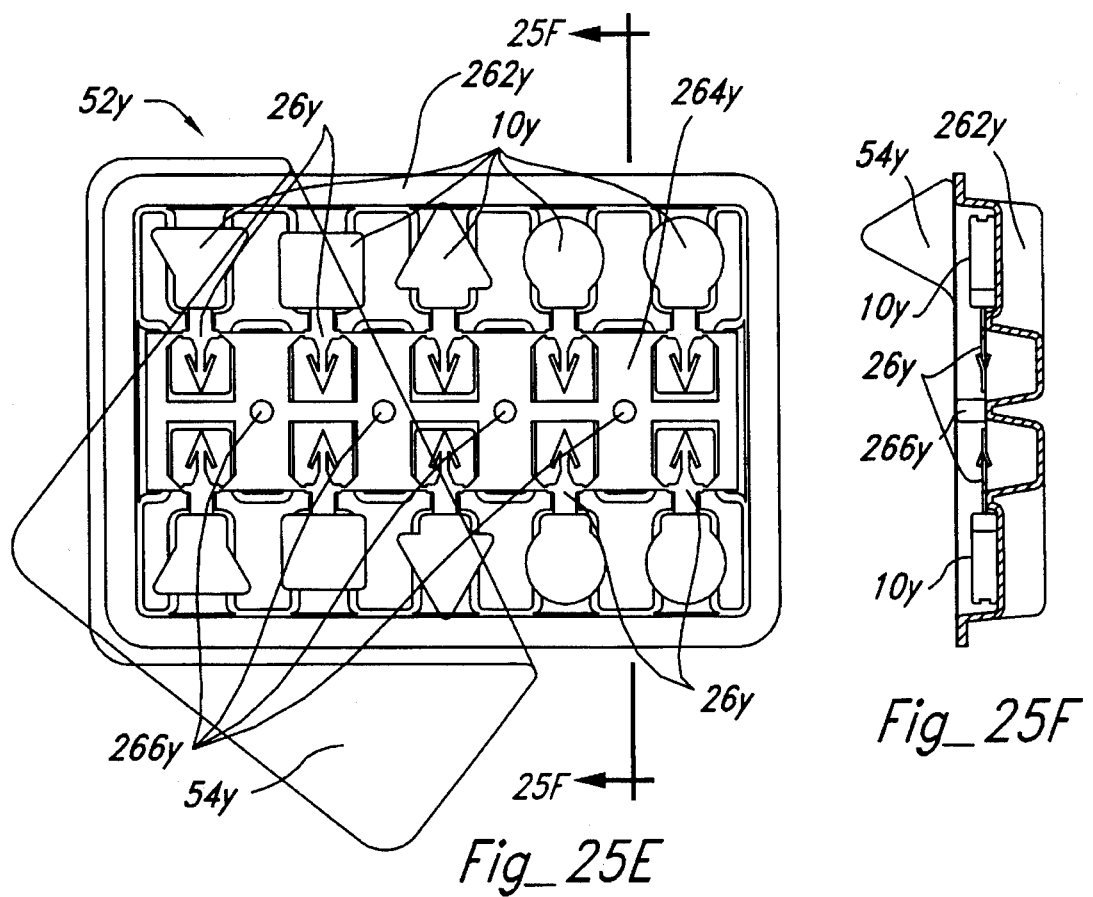

5,474,569

POST-SURGICAL GROSS PATHOLOGY SPECIMEN MARKER

This is a continuation of application Ser. No. 07/853,505, filed on Mar. 18, 1992, now abandoned.

INTRODUCTION

The present invention relates to devices which are used to mark or tag medical specimens, and more particularly used to mark and tag post-surgical gross pathology specimens.

BACKGROUND OF THE INVENTION

Successful removal of tumors from a patient's body requires an accurate evaluation of the excised tissue boundaries. To ensure that the entire tumor is removed, an adequate amount of healthy tissue surrounding the tumor is also extracted. The success of the surgery and the patient outcome is directly related to excision of the entirety of the tumor with an adequate healthy tissue boundary. This method is applicable to virtually all tumors in the human body. For example, this method is applicable to the removal of breast tumors (lumpectomy, quadrenectomy). Radical mastectomy was the mainstay of surgery for treatment of breast carcinoma until the 1970's when breast preservation surgery became an alternative. In the past two decades breast preservation surgery is chosen more and more by women. Successful removal of breast tumors requires an accurate evaluation of the removed tissue boundaries as described above.

In addition, accurate evaluation of the pathophysiology of tumor spread requires the dissection and analysis of lymph nodes.

To date, the demarcation of surfaces of tissue specimens (including tumors and nodes) may be performed by the surgeon after resection. The surgeon generally may attach to the surfaces of a tissue specimen sutures of various lengths which include various knots. The various lengths and knots of each suture convey to the pathologist the orientation of the gross pathology specimen in the patient's body. Unfortunately, this process is rarely performed because it is time consuming and requires detailed oral and/or written communications between surgeons and pathologists which often result in frustrations between the two professionals.

SUMMARY OF THE INVENTION

A set of specially designed devices is presented to address the inadequacies of the current methods of indicating the various surfaces of a volume of tissue composing a pathology specimen. The devices comprise clip-like markers which can easily be attached to pathology specimen surfaces by the surgeon in seconds. This process significantly facilitates the pathologist's understanding of the original orientation of the specimen in the patient's body and, therefore, significantly improves the accuracy of the pathologist's evaluation of the specimen.

The devices are easily fastened to a specimen being surgically removed. A surgeon may use six such devices to indicate the six sides of a volume of tissue (i.e. anterior, posterior, lateral, medial, superior and inferior). When such devices are attached to the tissue specimen the pathologist, at the time of evaluation, can easily determine the original orientation of the gross specimen in the patient's body. After evaluating the specimen, the pathologist is able to meaningfully and accurately communicate to the surgeon which, if any, of the healthy tissue boundaries were invaded.

The preferred embodiment of the set of devices comprises several small clip-like devices each comprising a pair of steel grippers, two tool engagement areas, and a plastic shell. The devices may be used by manipulating forceps or other similar instruments. For example, a surgeon may easily retrieve the marker from its packaging with forceps, position the marker on the specimen and clamp it shut thereby clipping it onto the specimen all within a matter of seconds. Thus, the procedure is quickly and easily accomplished.

BRIEF DESCRIPTION OF THE DRAWINGS

FIG. 1A is a plan view of a preferred embodiment of a specimen marker in an open position.

FIG. 1B is a plan view of the specimen marker of FIG. 1A in a closed position.

FIG. 1C is a side view of the specimen marker.

FIG. 1D is a plan view of the specimen marker in an open position with its front cover off.

FIG. 1E is a cross-sectional view of the specimen marker taken along line 1E—1E in FIG. 1B.

FIG. 1F is a plan view of the gripper element of the specimen marker.

FIG. 1G is a plan view of a specimen marker holder with six specimen markers held therein and with the holder cover partially opened.

FIG. 1H is a side view of the specimen marker holder with the holder cover partially opened.

FIG. 1I is a cross-sectional view of the specimen marker holder with specimen markers held therein taken along line 1I—1I in FIG. 1G.

FIG. 1J is a plan view of a marker holder front frame.

FIG. 1K is a back view of the marker holder front frame.

FIG. 1L is a plan view of a marker holder rear frame.

FIG. 1M is a back view of the marker holder rear frame.

FIG. 1N is a perspective view of the marker holder rear frame, one pair of gripper elements, and the marker holder front frame as they are being assembled to form a specimen marker and a specimen marker holder.

FIG. 2A is a plan view of a second embodiment of a specimen marker in an open position.

FIG. 2B is a plan view of the specimen marker of FIG. 2A in a closed position.

FIG. 2C is a side view of the specimen marker.

FIG. 2D is a plan view of the specimen marker in an open position with its front cover off.

FIG. 2E is a cross-sectional view of the specimen marker taken along line 2E—2E in FIG. 2B.

FIG. 3A is a plan view of a third embodiment of a specimen marker in an open position.

FIG. 3B is a plan view of the specimen marker of FIG. 3A in a closed position.

FIG. 3C is a plan view of the specimen marker in an open position with its front cover off.

FIG. 4A is a plan view of a fourth embodiment of a specimen marker in an open position.

FIG. 4B is a plan view of the specimen marker of FIG. 4A in a closed position.

FIG. 4C is a side view of the specimen marker in a closed position.

FIG. 4D is a plan view of a gripper element of the specimen marker.

FIG. 4E is a cross-sectional view of the specimen marker taken along line 4E—4E in FIG. 4B.

FIG. 4F is a cross-sectional view of the specimen marker in an open position.

FIG. 5A is a plan view of a fifth embodiment of a specimen marker in an open position.

FIG. 5B is a plan view of the specimen marker of FIG. 5A in a closed position.

FIG. 5C is a side view of the specimen marker.

FIG. 5D is a cross-sectional view of the specimen marker in an open position.

FIG. 5E is a cross-sectional view of the specimen marker taken along line 5E—5E in FIG. 5B.

FIG. 6A is a plan view of a sixth embodiment of a specimen marker in an open position.

FIG. 6B is a plan view of the specimen marker of FIG. 6A in a closed position.

FIG. 6C is a side view of the specimen marker.

FIG. 6D is a plan view of a gripper section of the specimen marker with the front gripper section off.

FIG. 6E is a cross-sectional view of the specimen marker taken along line 6E—6E in FIG. 6B.

FIG. 8A is a plan view of an eighth embodiment of a specimen marker in an open position.

FIG. 8B is a plan view of the specimen marker of FIG. 8A in a closed position.

FIG. 8C is a side view of the specimen marker.

FIG. 8D is a cross-sectional view of the specimen marker in an open position.

FIG. 8E is a cross-sectional view of the specimen marker taken along line 8E—8E in FIG. 8B.

FIG. 9A is a plan view of a ninth embodiment of a specimen marker in an open position.

FIG. 9B is a plan view of the specimen marker of FIG. 9A in a closed position.

FIG. 9C is a side view of the specimen marker.

FIG. 9D is a cross-sectional view of the specimen marker in a closed position taken along line 9D—9D in FIG. 9C.

FIG. 9E is a cross-sectional view of the specimen marker taken along line 9E—9E in FIG. 9B.

FIG. 10A is a plan view of a tenth embodiment of a specimen marker in an open position.

FIG. 10B is a plan view of the specimen marker of FIG. 10A in a closed position.

FIG. 10C is a side view of the specimen marker.

FIG. 10D is a plan view of the specimen marker in a closed position with its front shell off.

FIG. 10E is a cross-sectional view of the specimen marker taken along line 10E—10E in FIG. 10B.

FIG. 11A is a plan view of an eleventh embodiment of a specimen marker in an open position.

FIG. 11B is a plan view of the specimen marker of FIG. 11A in a closed position.

FIG. 11C is a side view of the specimen marker.

FIG. 12A is a plan view of a twelfth embodiment of a specimen marker in an open position.

FIG. 12B is a plan view of the specimen marker of FIG. 12A in a closed position.

FIG. 12C is a side view of the specimen marker.

FIG. 13A is a plan view of a thirteenth embodiment of a specimen marker in an open position.

FIG. 13B is a plan view of the specimen marker of FIG. 13A in a closed position.

FIG. 13C is a side view of the specimen marker.

FIG. 15A is a plan view of a fifteenth embodiment of a specimen marker in an open position.

FIG. 15B is a plan view of the specimen marker of FIG. 15A in a closed position.

FIG. 15C is a top view of the specimen marker in an open position.

FIG. 15D is a top view of the specimen marker in a closed position.

FIG. 15E is a back view of the specimen marker in an open position.

FIG. 16A is a plan view of a sixteenth embodiment of a specimen marker in an open position.

FIG. 16B is a plan view of the specimen marker of FIG. 16A in a closed position.

FIG. 16C is a side view of the specimen marker in a closed position.

FIG. 16D is a cross-sectional view of the specimen marker in an open position.

FIG. 17A is a plan view of a seventeenth embodiment of a specimen marker in an open position.

FIG. 17B is a plan view of the specimen marker of FIG. 17A in a closed position.

FIG. 17C is a side view of the specimen marker in a closed position.

FIG. 17D is a cross-sectional view of the specimen marker in an open position.

FIG. 18A is a plan view of an eighteenth embodiment of a specimen marker in an open position.

FIG. 18B is a plan view of the specimen marker of FIG. 18A in a closed position.

FIG. 18C is a top view of the specimen marker in an open position.

FIG. 18D is a cross-sectional view of the specimen marker in an open position taken along line 18D—18D in FIG. 18A.

FIG. 19A is a plan view of a nineteenth embodiment of a specimen marker in an open position.

FIG. 19B is a plan view of the specimen marker of FIG. 19A in a closed position.

FIG. 19C is a side view of the specimen marker in a closed position.

FIG. 19D is a top view of the specimen marker in an open position.

FIG. 19E is a top view of the specimen marker in a closed position.

FIG. 20A is a plan view of a twentieth embodiment of a specimen marker in an open position.

FIG. 20B is a plan view of the specimen marker of FIG. 20A in a closed position.

FIG. 20C is a top view of the specimen marker in a closed position.

FIG. 20D is a rear view of the specimen marker in an open position.

FIG. 21A is a plan view of a twenty-first embodiment of a specimen marker in an open position.

FIG. 21B is a plan view of the specimen marker of FIG. 21A in a closed position.

FIG. 21C is a side view of the specimen marker.

FIG. 21D is a plan view of the specimen marker in an open position with its front cover off.

FIG. 21E is a cross-sectional view of the specimen marker taken along line 21E—21E in FIG. 21B.

FIG. 21F is a plan view of the specimen marker in an open position and a custom tool as the custom tool is inserted into the marker in preparation of closing the specimen marker.

FIG. 21G is a plan view of the specimen marker in an open position and the custom tool of FIG. 21F while the custom tool is in a first position.

FIG. 21H is a plan view of the specimen marker in a closed position and the custom tool while the custom tool is in a second position.

FIG. 21I is a plan view of the specimen marker in a closed position and the custom tool as the custom tool is removed from the marker after closing the marker.

FIG. 22A is a plan view of a twenty-second embodiment of a specimen marker in an open position and a custom tool in a first position.

FIG. 22B is a plan view of the specimen marker of FIG. 22A in a closed position with its front cover off and the custom tool of FIG. 22A in a second position.

FIG. 23A is a plan view of a twenty-third embodiment of a specimen marker in an open position.

FIG. 23B is a plan view of the specimen marker of FIG. 23A in a closed position.

FIG. 23C is a side view of the specimen marker.

FIG. 23D is a plan view of the specimen marker in an open position with its front cover off.

FIG. 23E is a cross-sectional view of the specimen marker taken along line 23E—23E in FIG. 23B.

FIG. 23F is a plan view of the specimen marker in an open position and a custom tool as the specimen marker is inserted onto the custom tool in preparation of closing the marker.

FIG. 23G is a plan view of the specimen marker in an open position and the custom tool of FIG. 23F while the custom tool is in a first position.

FIG. 23H is a plan view of the specimen marker in a closed position and the custom tool while the custom tool is in a second position.

FIG. 23I is a plan view of the specimen marker in a closed position and the custom tool as the custom tool is removed from the marker after closing the marker.

FIG. 24A is a plan view of a twenty-fourth embodiment of a specimen marker in an open position.

FIG. 24B is a plan view of the specimen marker of FIG. 24A in a closed position.

FIG. 24C is a top view of the specimen marker in an open position.

FIG. 24D is a plan view of the specimen marker in an open position with its cover opened.

FIG. 24E is a cross-sectional view of the specimen marker taken along line 24E—24E in FIG. 24B.

FIG. 24F is a top view of the specimen marker cover in an open position.

FIG. 25A is a plan view of a twenty-fifth embodiment of a specimen marker as it is applied to a specimen.

FIG. 25B is a side view of the specimen marker of FIG. 25A.

FIG. 25C is a cross-sectional view of the specimen marker taken along line 25C—25C in FIG. 25B.

FIG. 25D is a cross-sectional view of the specimen marker taken along line 25D—25D in FIG. 25A.

FIG. 25E is a plan view of a specimen marker holder with ten specimen markers held therein and with the holder cover partially opened.

FIG. 25F is a cross-sectional view of the specimen marker holder of FIG. 25E with specimen markers held therein taken along line 25F—25F in FIG. 25E.

DESCRIPTION OF THE PREFERRED EMBODIMENT

Figure 7A:
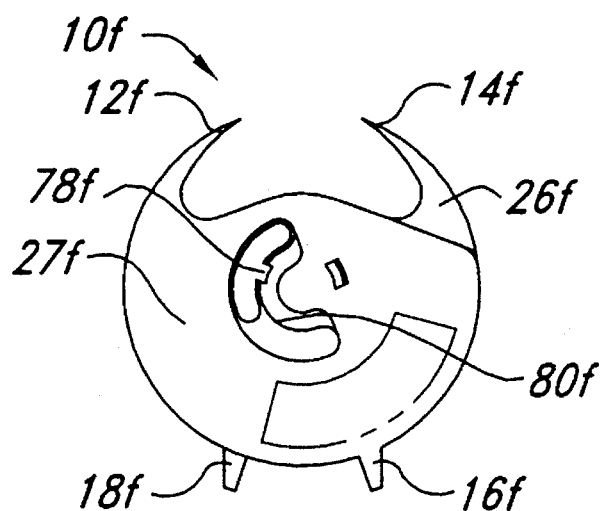
FIG. 7A is a plan view of a seventh embodiment of a specimen marker in an open position.

Turning now to the drawings in detail, FIGS. 1A–1E show a preferred embodiment of the present invention in the form of a specimen marker 10. The specimen marker 10 generally comprises two flat gripper elements 26 and 27 (one gripper element 26 is shown in detail in FIG. 1F), a front shell cover 22 and a rear shell cover 24 (see FIG. 1C).

FIG. 1F shows the design of gripper element 26. Both gripper elements 26 and 27 are of the design and shape shown in FIG. 1F. The gripper elements 26 and 27 are merely oppositely placed between the shell covers 22 and 24 (see FIG. 1D).

As shown in FIG. 1F, gripper element 26 is shaped somewhat like a question mark ("?") comprising a head 1, a body 2, and a tail 3. The head 1 includes two arcuate edges 4 and 5 which form a sharp arcuate gripper point 14. The body 2, which is a broader continuation of the arcuate edges 4 and 5, includes a slot cut-out comprising a stop pin slot 28 and a circular cut-out comprising a pivot pin aperture 30. The tail 3 extends out from the body 2 and comprises a rounded gripper handle 18 with an elliptical cut-out comprising a tool engagement hole 20.

Each specimen marker 10 comprises two such gripper elements 26 and 27 (see FIG. 1D): one element 26 comprising a first gripper point 14, a stop pin slot 28, a pivot pin aperture 30, a first gripper handle 18, and a tool engagement hole 20; and the other element 27 comprising a second gripper point 12, a stop pin slot 28 (not shown), a pivot pin aperture 30 (not shown), a second gripper handle 16, and a tool engagement hole 20.

The gripper elements 26 and 27 are preferably made from stainless steel and are preferably formed by photo-etching the metal. As shown in FIG. 1F, an identification mark 62 may also be photo-etched on or through the gripper elements 26 and 27. Identification mark 62 is visible whether the specimen marker 10 is in an open or closed position, and is visible when viewed as an X-ray image. The photo-etching process allows the gripper elements 26 and 27 to be manufactured such that gripper points 12 and 14 are very sharp.

Each specimen marker 10 also comprises a front shell cover 22 and a rear shell cover 24 between which the gripper elements 26 and 27 are movably sandwiched (FIGS. 1C and 1E). The shell covers 22 and 24 are generally shaped like semi-circles, each including a rounded edge 23 and a flat edge 25. The shell covers 22 and 24 are preferably made from injection molded plastic.

The marker shell covers 22 and 24 and the gripper elements 26 and 27 are fairly small and flat such that an assembled marker 10, in a closed position, has an approximate length of 0.79 inches, width of 0.48 inches, and thickness of 0.10 inches. Although approximate dimensions are given, the specimen marker 10 in general may range in size with the preferred range being from about 0.1 square inches to about 1.5 square inches with a thickness of up to 0.25 inches.

The shell covers 22 and 24 each include an inner surface 64 (FIG. 1K) and 46 (FIG. 1L) respectively and an outer surface 48 (FIG. 1J) and 66 (FIG. 1M) respectively. In the preferred embodiment, one or both of the outer surfaces 48 and 66 include raised molded identification marks 63 to allow the marker 10 to indicate information (FIG. 1J). Identification marks 63 are suitable for hot stamping with a contrasting color to increase the visibility and legibility of the identification mark.

As shown in FIG. 1D, the inner surface 46 of the rear shell cover 24 comprises a stop pin 32 and a pivot pin 34 which includes a retainer pin aperture 36 (also see FIG. 1E). Also shown in FIG. 1D, the gripper elements 26 and 27 fit over and around the features of the rear shell cover 24. More specifically, the stop pin slots 28 of the gripper elements 26 and 27 fit over the stop pin 32 and the pivot pin apertures 30 of the gripper elements 26 and 27 fit over the pivot pin 34. The gripper elements 26 and 27 are positioned between the shell covers 22 and 24 such that the gripper handles 16 and 18 extend from the covers 22 and 24 at the rounded edge 23 and the gripper points 12 and 14 extend from the shell covers 22 and 24 at the flat edge 25 such that the gripper points 12 and 14 oppose each other (FIGS. 1A and 1B).

As shown in FIG. 1E, the shell covers 22 and 24 complement each other. The inner surface 64 of the front shell cover 22 is adapted to match the features of the inner surface 46 of the rear shell cover 24. Specifically, the front shell cover includes a retainer pin 38 which fits into the retainer pin aperture 36 of the pivot pin 34 of the rear shell cover 24, a pivot pin recess 40 and a stop pin recess 42 which match and fit over the pivot pin 34 and the stop pin 32 of the rear shell cover respectively. These pin and recess (or aperture) couplings (38/36, 34/40, and 32/42) allow the shell covers 22 and 24 to be fastened to one another with the gripper elements 26 and 27 sandwiched between them in the positions described above.

The specimen marker 10 attaches to a specimen by:

(1) holding the marker 10 and positioning the gripper points 12 and 14 against the surface of a specimen desired to be marked (this can be accomplished by using a tool, such as forceps, to engage the tool engagement holes 20 in handles 16 and 18);

(2) attaching the marker 10 by forcing the gripper handles 16 and 18 toward each other, thereby forcing the gripper points 12 and 14 to pivot or arc toward each other such that a portion of the specimen desired to be marked may be pinched between or pierced by the points 12 and 14 such that the marker 10 will remain attached to the specimen, and (3) releasing the marker 10 (by withdrawing the tool, if one is used, from the tool engagement holes 20).

Under normal circumstances, the gripper points 12 and 14 will cut into or penetrate the specimen surface thereby locking the marker 10 to the specimen.

When a marker 10 is placed onto a specimen, as described above, the gripper handles 16 and 18 are forced toward each other. This action causes the stop pin slots 28 of the gripper elements 26 and 27 to slide along the stop pin 32 of the rear shell cover 24. This action also causes the gripper elements 26 and 27 to rotate about the pivot pin 34 (gripper element 26 rotating in a counter-clockwise motion and gripper element 27 rotating in a clockwise motion). However, the stop pin 32 and the stop pin slots 28 limit the rotations to positions where the gripper points 12 and 14 meet or overlap somewhat (as shown in FIG. 1B). Thus, the gripper elements 26 and 27 have limited positions.

As shown in FIGS. 1D and 1F, the stop pin slots 28 of the gripper elements 26 and 27 may have enlarged areas 44 at both ends. The width of the slots 28 is slightly smaller than the diameter of the stop pin 32. The diameters of the enlarged areas 44 are either substantially the same as or larger than the diameter of the stop pin 32 and larger than the width of the slots 28. Thus, the enlarged areas 44 form detents for the stop pin 32 which cause the gripper elements 26 and 27 to remain in positions where the stop pin 32 is located in one of the enlarged areas 44. Therefore, the enlarged areas 44 act as detents and cause the gripper elements 26 and 27 to remain in either an open position (where the gripper points 12 and 14 are apart from each other, as in FIG. 1A) or a closed position (where the gripper points 12 and 14 are near each other, as in FIG. 1B).

Turning to FIGS. 1G–1I, a preferred packaging apparatus 50 for packaging specimen markers 10 is shown. The packaging apparatus 50 preferably contains six specimen markers 10 in a ready to use state (see FIG. 1G). The packaging apparatus 50 is rectangular in shape and comprises a marker holder 52, an optional peel-off front cover sheet 54, and an optional peel-off rear cover sheet 56 (see FIGS. 1G–1I).

In addition to serving as a container for the specimen markers 10, the marker holder 52 is integral in the manufacture of the specimen markers 10. As shown in FIGS. 1J–1N, the marker holder 52 comprises a marker holder front frame 58 (FIGS. 1I–1K and 1N) and a marker holder rear frame 60 (FIGS. 1I and 1L–1N). The marker holder front frame 58 and rear frame 60 are preferably made from injection molded plastic. The marker holder front frame 58 is preferably molded with a set of six front shell covers 22 molded thereto (FIGS. 1J and 1K). The front shell covers 22 are each attached to the marker holder front frame 58 at a break-off point 74 which is also a gate for molding (FIGS. 1I–1K). Each break-off point 74 comprises a reduced thickness of plastic such that each front shell cover 22 may be easily detached from the marker holder front frame 58.

As shown in FIGS. 1K and 1N, the marker holder front frame 58 includes an inner surface 68 (which corresponds to the front shell cover inner surface 64) upon which are molded attachment posts 70. The attachment posts 70 allow the marker holder front frame 58 to be attached to the marker holder rear frame 60 thereby forming the marker holder 52.

Turning to FIGS. 1L–1N, the marker holder rear frame 60 is preferably molded with a set of six rear shell covers 24 molded thereto. Each rear shell cover 24 is attached to the marker holder rear frame 60 at a break-off point 76 which is also a gate for molding (FIG. 1M). Each break-off point 76 comprises a reduced thickness of plastic such that each rear shell cover 24 may be easily removed from the marker holder rear frame 60.

The marker holder rear frame 60 includes attachment apertures 72 which are molded therethrough (see FIGS. 1L–1N). As shown in FIG. 1N, the attachment apertures 72 correspond to and engage the attachment posts 70 such that the marker holder front frame 58 may be attached to the marker holder rear frame 60 thereby forming the marker holder 52. As shown in FIG. 1N, before the marker holder front frame 58 and rear frame 60 are attached to each other, gripper elements 26 and 27 are placed on the pivot pins 34 of each rear shell cover 24 such that when the marker holder front frame 58 and rear frame 60 are attached, the specimen markers 10 are thereby assembled. FIG. 1G shows an assembled marker holder 52 (i.e. front frame 58 and rear frame 60 attached with gripper elements 26 and 27 in place such that specimen markers 10 are assembled).

As noted above, the packaging apparatus 50 includes optional peel-off cover sheets 54 and 56 (see FIGS. 1G–1I). The cover sheets 54 and 56 may be made of materials commonly used to fabricate pouches suitable for preserving the sterility of any contained items. Thus, the packaging apparatus 50 may serve as a complete, self-contained package for sterilizing and protecting the enclosed specimen markers 10.

FIGS. 2A–2E show a second embodiment of the invention in the form of a specimen marker 10a. The description of specimen marker 10 provided above (see FIGS. 1A–1N) is applicable to specimen marker 10a. Therefore, identifying numbers which correspond to those used in the description and drawings of specimen marker 10 (FIGS. 1A–1E) have been used in the description and drawings of specimen marker 10a (FIGS. 2A–2E).

As shown in FIGS. 2A–2E, specimen marker 10a generally comprises two flat gripper elements 26a and 27a, a front shell cover 22a, and a rear shell cover 24a (FIG. 2C).

FIG. 2D shows the design of gripper element 26a. Each gripper element 26a and 27a is of the design and shape shown in FIG. 2D. The gripper elements 26a and 27a are merely oppositely placed between the shell covers 22a and 24a (FIG. 2D).

As shown in FIG. 2D, gripper element 26a is shaped somewhat like a question mark ("?") and includes two arcuate edges 4a and 5a which form a sharp arcuate gripper point 14a, a slot cut-out comprising a stop pin slot 28a, a circular cut-out comprising a pivot pin aperture 30a, and a rounded gripper handle 18a with an elliptical cut-out comprising a tool engagement hole 20a.

Each specimen marker 10a comprises two such gripper elements 26a and 27a (FIG. 2D). As shown in FIG. 2D, each gripper element 26a comprises a first gripper point 14a, a first gripper handle 18a, a tool engagement hole 20a, a stop pin slot 28a, and a pivot pin aperture 30a. Each gripper element 27a comprises a second gripper point 12a, a second gripper handle 16a, a tool engagement hole 20a, a stop pin slot 28a (not shown), and a pivot pin aperture 30a (not shown).

The gripper elements 26a and 27a are preferably made from stainless steel and are preferably formed by photo-etching the metal. An identification mark (not shown) may also be photo-etched on the gripper elements 26a and 27a. The photo-etching process allows the gripper elements 26a and 27a to be manufactured such that gripper points 12a and 14a are sharp.

Each specimen marker 10a also comprises a front shell cover 22a and a rear shell cover 24a between which the gripper elements 26a and 27a are movably sandwiched (FIGS. 2C and 2E). The shell covers 22a and 24a are shaped like semi-circles, each including a rounded edge 23a and a flat edge 25a. The shell covers 22a and 24a are preferably made from injection molded plastic.

The marker shell covers 22a and 24a and the gripper elements 26a and 27a are fairly small and flat such that an assembled marker 10a, in a closed position, falls within the preferred range of sizes (described above).

The shell covers 22a and 24a each include an inner surface 64a and 46a respectively and an outer surface 48a and 66a respectively (FIG. 2E). The shell cover outer surfaces 48a and 66a may include identification marks to allow information to be indicated on the marker 10a.

As shown in FIG. 2D, the inner surface 46a of the rear shell cover 24a comprises a stop pin 32a and a pivot pin 34a which includes a triangular retainer pin aperture 36a (also see FIG. 2E). The gripper elements 26a and 27a fit over and around the features of the rear shell cover 24a (FIG. 2D). More specifically, the stop pin slots 28a of the gripper elements 26a and 27a fit over the stop pin 32a and the pivot pin apertures 30a of the gripper elements 26a and 27a fit over the pivot pin 34a. The gripper elements 26a and 27a are positioned between the shell covers 22a and 24a such that the gripper handles 16a and 18a extend from the shell covers 22a and 24a at the rounded edge 23a and the gripper points 12a and 14a extend from the shell covers 22a and 24a at the flat edge 25a such that the gripper points 12a and 14a oppose each other (FIGS. 2A and 2B).

As shown in FIG. 2E, the shell covers 22a and 24a complement each other. The inner surface 64a of the front shell cover 22a is adapted to match the features of the inner surface 46a of the rear shell cover 24a in such a way so as to allow the shell covers 22a and 24a to be fastened to one another with the gripper elements 26a and 27a sandwiched between them. Specifically, the front shell cover 22a includes a triangular retainer pin 38a which fits into the triangular retainer pin aperture 36a of the pivot pin 34a of the rear shell cover 24a, a pivot pin recess 40a and a stop pin recess 42a which match and fit over the pivot pin 34a and the stop pin 32a of the rear shell cover 24a respectively. The triangular retainer pin 38a inserts into the triangular retainer pin aperture 36a so as to provide proper positioning of the shell covers 22a and 24a when the marker 10a is assembled.

As is evident from FIGS. 2A–2D, specimen marker 10a functions by forcing the gripper handles 16a and 18a toward each other. This action causes the stop pin slots 28a of the gripper elements 26a and 27a to slide along the stop pin 32a of the rear shell cover 24a. This action also causes the gripper elements 26a and 27a to rotate around the pivot pin 34a such that gripper element 26a rotates in a counter-clockwise direction and gripper element 27a rotates in a clockwise direction. However, the stop pin 32a and the stop pin slots 28a limit the rotations to a position where the gripper points 12a and 14a meet or overlap somewhat (as shown in FIG. 2B). As the gripper points 12a and 14a approach each other, a portion of the specimen sought to be marked may be pinched between or pierced by the points 12a and 14a thereby attaching the specimen marker 10a to the specimen and marking it.

As shown in FIG. 2D, the stop pin slots 28a of the gripper elements 26a and 27a may have enlarged areas 44a at both ends. The width of the slots 28 is slightly smaller than the diameter of the stop pin 32. The diameters of the enlarged areas 44 are either substantially the same as or larger than the diameter of the stop pin 32 and larger than the width of the slots 28. Thus, the enlarged areas 44a form detents for the stop pin 32a which cause the gripper elements 26a and 27a to remain in positions where the stop pin 32a is located in one of the enlarged areas 44a. Therefore, the enlarged areas 44a act as detents and cause the gripper elements 26a and 27a to remain in either an open position (where the gripper points 12a and 14a are furthest from each other, as shown in FIG. 2A) or a closed position (where the gripper points 12a and 14a are closest to each other, as shown in FIG. 2B).

FIGS. 3A–3C show a third embodiment of the present invention in the form of a specimen marker 10b. Specimen marker 10b is shaped similar to specimen marker 10 (described above). Specimen marker 10b comprises two flat gripper elements 26b and 27b, a front shell cover 22b, and a rear shell cover 24b (not shown). Each gripper element 26b and 27b is of the same design and shape. The gripper elements 26b and 27b are merely oppositely placed between the shell covers 22b and 24b. The main difference between specimen marker 10b and specimen marker 10 is the manner in which the rotation of the gripper elements 26b and 27b is limited.

Gripper element 26b is shaped similar to gripper element 26. That is, it is shaped similar to a question mark ("?") and includes two arcuate edges 4b and 5b which form an arcuate gripper point 14b, a circular cut-out comprising a pivot pin aperture 30b, and a rounded gripper handle 18b with an elliptical cut-out comprising a tool engagement hole 20b (FIG. 3C). However, gripper element 26b also includes edge notches 80b (FIG. 3C).

Each specimen marker 10b comprises two such gripper elements 26b and 27b. Thus, each specimen marker 10b includes a first gripper point 14b, a second gripper point 12b, a first gripper handle 18b, a second gripper handle 16b, tool engagement holes 20b, edge notches 80b, and pivot pin apertures 30b.

The gripper elements 26b and 27b are preferably made by photo-etching stainless steel. An identification mark 62b may be photo-etched on the gripper elements 26b and 27b (FIGS. 3A and 3B).

Each specimen marker 10b also comprises a shell cover arrangement as does specimen marker 10 (i.e. including a front shell cover 22b and a rear shell cover 24b (which includes a pivot pin 34b) which fit together such that the gripper elements 26b and 27b are movably sandwiched between the shell covers 22b and 24b). However, the shell covers 22b and 24b are circularly shaped with a rounded edge 23b and include raised areas along portions of the rounded edge 23b defining two stops 78b which are positioned directly opposite one another (see FIGS. 3A–3C). The gripper elements 26b and 27b are positioned between the shell covers 22b and 24b such that the gripper handles 16b and 18b extend from the shell covers 22b and 24b at one pivot edge 80b and the gripper points 12b and 14b extend from the shell covers 22b and 24b at the opposite stops 78b. In addition, the edge notches 80b of the gripper elements 26b and 27b engage the stops 78b of the shell covers 22b and 24b in such a way that the notch 80b and stop 78b arrangement limits the gripper element 26b and 27b movement (explained further below). The edge notch 80b and stop 78b arrangement is the main difference between specimen marker 10b and specimen marker 10.

The shell covers 22b and 24b are preferably made from injection molded plastic. The assembled specimen marker 10b is small and falls within the preferred range of sizes (described above) when it is in a closed position.

As is evident from FIGS. 3A–3C, specimen marker 10b functions by forcing the gripper handles 16b and 18b toward each other. This action causes the gripper elements 26b and 27b to rotate around the pivot pin 34b such that gripper element 26b moves in a counter-clockwise direction and gripper element 27b moves in a clockwise direction (thereby causing the gripper points 12b and 14b to approach each other) and the edge notches 80b slide along the stops 78b. The edge notches 80b are of limited length. The stops 78b can slide only along the limited length of the edge notches 80b. Thus, the stops 78b of the shell covers 22b and 24b and the edge notches 80b of the gripper elements 26b and 27b limit the rotation of the gripper elements 26b and 27b.

As the gripper elements 26b and 27b rotate and the gripper points 12b and 14b thereby approach each other, a portion of the specimen sought to be marked may be pinched between or pierced by the gripper points 12b and 14b thereby attaching the specimen marker 10b to the specimen and marking it.

FIGS. 4A–4F show a fourth embodiment of the present invention in the form of a specimen marker 10c. Specimen marker 10c is shaped similar to specimen marker 10 (described above). Specimen marker 10c generally comprises two flat gripper elements 26c and 27c and a marker shell 110c (FIGS. 4A and 4B). Each gripper element 26c and 27c is of the same design and is merely placed opposite to the other on the marker shell 110c (FIG. 4F). The main differences between specimen marker 10c and specimen marker 10 are the design of the marker shell 110c and the manner of attaching and limiting the rotation of the gripper elements 26c and 27c.

As shown in FIG. 4E, the marker shell 110c is one molded piece comprising three sections: a front section 112c, a back section 114c, and a core section 116c. The front and back sections 112c and 114c sandwich the core 116c (FIG. 4E) and are substantially circular shaped (FIGS. 4A and 4B). The core 116c is also circular shaped with a outside edge defining a gripper element pivot surface 86c (FIGS. 4E and 4F) which includes indents 88c (FIG. 4F). The marker shell 110c is preferably made from injection molded plastic. Comparing specimen marker 10c to specimen marker 10: the front and back sections 112c and 114c take the place of the front and back shell covers 22 and 24, and the core 116c takes the place of the pivot pin 34.

As shown in FIG. 4D, gripper element 26c is shaped similar to gripper element 26 of specimen marker 10 (i.e. including a head 1c with two arcuate edges 4c and 5c which form an arcuate gripper point 14c, a body 2c with a circular opening comprising a pivot pin aperture 30c, and a tail 3c with a rounded gripper handle 18c and an elliptical cut-out comprising a tool engagement hole 20c). However, the body 2c of the gripper element 26c includes an opening 29c and a pivot pin aperture 30c which is defined by an edge 31c with tabs 91c (FIG. 4D).

The openings 29c in the body 2c of the gripper elements 26c and 27c provide means for attaching the gripper elements 26c and 27c to the marker shell 110c. The openings 29c may be dimensioned slightly smaller than the diameter of the core 116c. the slight flexibility of the gripper elements 26c and 27c allows them to be snapped onto the core 116c such that they are retained on the core 116c by an over-center condition.

As shown in FIGS. 4A and 4B, each specimen marker 10c includes two gripper elements 26c and 27c. Thus, each marker 10c includes a first gripper point 14c, a second gripper point 12c, a first gripper handle 18c, a second gripper handle 16c, tool engagement holes 20c, and pivot pin apertures 30c and edges 31c. The gripper elements 26c and 27c are preferably made by photo-etching stainless steel. An identification mark 62c may also be photo-etched thereon (see FIGS. 4A, 4B, and 4D).

The gripper elements 26c and 27c are positioned on the marker shell core 116c such that the pivot pin edges 31c of the gripper elements 26c and 27c are in contact with the gripper pivot surface 86c (FIG. 4F). This arrangement allows the gripper elements 26c and 27c to slide along the gripper pivot surface 86c as the specimen marker 10c is adapted from an open position (FIG. 4A) to a closed position (FIG. 4B) by forcing the gripper handles 16c and 18c toward each other. The gripper elements 26c and 27c slide along the gripper pivot surface 86c such that gripper element 26c rotates counter-clockwise and gripper element 27c rotates clockwise around the marker shell core 116c. This action causes the gripper points 12c and 14c to move toward each other such that a portion of a specimen may be pinched between or pierced by the two points 12c and 14c and the specimen marker 10c may thereby be attached to and mark the specimen.

As shown in FIG. 4F, the rotations are limited by the interaction of the tabs 91c on the gripper pivot pin edges 31c and the indents 88c on the marker shell core 116c. The tabs 91c catch in the indents 88c thereby causing the gripper elements 26c and 27c to remain in positions where the tabs 91c are located in the indents 88c. As the gripper elements 26c and 27c are rotated around the marker shell core 116c, the tabs 91c engage the indents 88c at points where the gripper elements 26c and 27c are in one of two positions: either where the gripper points 12c and 14c are in an open position (FIG. 4A) or where the gripper points 12c and 14c are in a closed position (FIG. 4B).

The assembled specimen marker 10c is small such that it falls within the preferred range of sizes (described above) when in a closed position.

Turning now to FIGS. 5A–5E, a fifth embodiment of the present invention in the form of a specimen marker 10d is shown. Specimen marker 10d is shaped similar to specimen marker 10c (described above). As shown in FIGS. 5A–5C, specimen marker 10d comprises a marker shell 110d and two wire gripper elements 84d and 85d. Each wire gripper element 84d and 85d is of the same design and is merely placed opposite to the other on the marker shell 110d. The main difference between specimen marker 10c and specimen marker 10d is the design of the wire gripper elements 84d and 85d.

As shown in FIGS. 5D–5E, marker shell 110d is shaped similar to marker shell 110c (i.e. including circular front and back sections 112d and 114d which sandwich a circular core section 116d defining a gripper element pivot surface 86d). The marker shell 110d also includes indents 88d. The marker shell 110d is preferably made from injection molded plastic.

As shown in FIG. 5D, wire gripper element 84d is shaped similar to gripper element 26c (i.e. wire gripper element 84d includes a point 14d, a handle 18d, and a tool engagement hole 20d). The wire gripper element 84d is shaped to also include a tab 91d (FIG. 5D).

As shown in FIGS. 5A and 5B, each specimen marker 10d includes two wire gripper elements 84d and 85d. Thus, each marker 10d includes a first gripper point 14d, a second gripper point 12d, a first gripper handle 18d, a second gripper handle 16d, and tool engagement holes 20d (associated with each gripper handle 16d and 18d). The wire gripper elements 84d and 85d are preferably made from stainless steel wire having a diameter of approximately 0.015 inches.

The wire gripper elements 84d and 85d are positioned on the marker shell 110d such that the elements 84d and 85d slide along the gripper pivot surface 86d as the marker 10d is adapted from an open position (FIG. 5A) to a closed position (FIG. 5B) by forcing the gripper handles 16d and 18d toward each other. The wire gripper elements 84d and 85d slide along the gripper pivot surface 86d such that wire gripper element 84d rotates counterclockwise and wire gripper element 85d rotates clockwise around the marker shell core 116d. Furthermore, as the gripper points 12d and 14d approach each other, a portion of a specimen may be pinched between or pierced by the gripper points 12d and 14d such that the specimen marker 10d attaches to and marks the specimen.

The movement of the gripper wire 84d is limited by the indents 88d and 90d on the marker shell core 116d. When the tabs 91d catch in the indent 90d, the specimen marker 10d is held in an open position (as shown in FIGS. 5A and 5D). When the tabs 91d catch in the indent 88d, the specimen marker 10d is held in a closed position (as shown in FIG. 5B).

The assembled specimen marker 10d is small such that it falls within the preferred range of sizes (described above) when in a closed position.

A sixth embodiment of the present invention is shown in FIGS. 6A–6E in the form of a specimen marker 10e. Specimen marker 10e is similar to the specimen markers 10–10d described above. The main differences in marker 10e are the design and shape of the gripper elements 26e and 27e.

As shown in FIGS. 6A and 6B, specimen marker 10e comprises two gripper elements 26e and 27e. FIG. 6D shows the design of gripper element 26e. Both gripper elements 26e and 27e are of the same design and shape shown. Gripper element 26e comprises a first gripper point 14e, a first gripper handle 18e, a catch hook 78e, and an arcuate pivot edge 80e (FIG. 6D). Gripper element 27e comprises a second gripper point 12e, a second gripper handle 16e, a catch hook 78e (not shown), and an arcuate pivot edge 80e (FIGS. 6A and 6B). The gripper elements 26e and 27e may be rotated from an open position (FIG. 6A) to a closed position (FIG. 6B) by forcing the gripper handles 16e and 18e toward each other. As the gripper handles 16e and 18e move together the gripper points 12e and 14e also move toward each other such that a portion of a specimen (not shown) may be pinched between or pierced by the two points 12e and 14e and the specimen marker 10e may thereby be attached to a specimen.

Gripper elements 26e and 27e are oppositely mated to one another such that the catch hook 78e on each gripper element 26e hooks over the pivot edge 80e on each gripper element 27e and vice versa. The hook 78e and edge 80e arrangement is designed such that the catch hooks 78e may only travel along the pivot edge 80e. The hooks 78e and pivot edges 80e are designed such that the gripper elements 26e and 27e are limited to being placed in either an open position (FIG. 6A) or a closed position (FIG. 6B).

Gripper elements 26e and 27e are preferably made from injection molded plastic, but could also be metal. The marker 10e is small such that it falls within the preferred range of sizes (described above) when in a closed position.

Figure 7B:
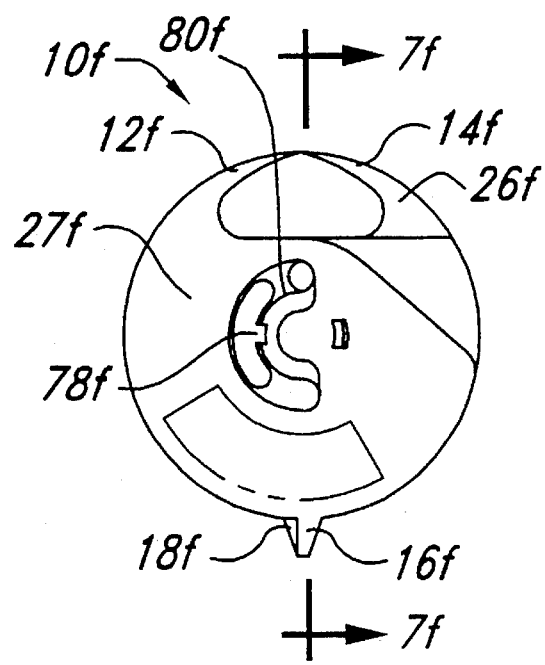
FIG. 7B is a plan view of the specimen marker of FIG. 7A in a closed position.
Figure 7C:
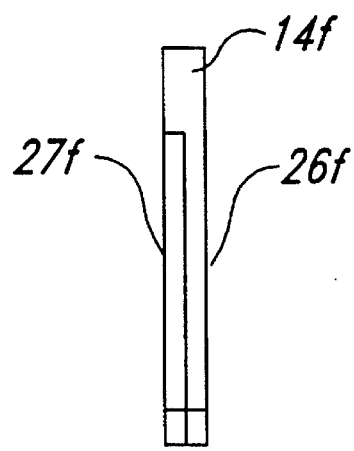
FIG. 7C is a side view of the specimen marker.

A seventh embodiment of the present invention is shown in FIGS. 7A–7C in the form of a specimen marker 10f. Specimen marker 10f is very similar to specimen marker 10e described above. The main difference in marker 10f is the relative open positions and the degree of possible angular displacement of gripper points 12f and 14f with respect to the design of gripper points 12e and 14e described above.

As shown in FIGS. 7A and 7B, specimen marker 10f comprises two gripper elements 26f and 27f. Both gripper elements 26f and 27f are of the same design and shape. Gripper element 26f comprises a first gripper point 14f, a first gripper handle 18f, a catch hook 78f, and an arcuate pivot edge 80f (FIGS. 7A and 7B). Gripper element 27f comprises a second gripper point 12f, a second gripper handle 16f, a catch hook 78f (not shown), and an arcuate pivot edge 80f (FIGS. 7A and 7B). The gripper elements 26f and 27f may be rotated from an open position (FIG. 7A) to a closed position (FIG. 7B) by forcing the gripper handles 16f and 18f toward each other. As the gripper handles 16f and 18f move together the gripper points 12f and 14f also move toward each other such that a portion of a specimen (not shown) may be pinched between or pierced by the two points 12f and 14f and the specimen marker 10f may thereby be attached to a specimen.

Gripper elements 26f and 27f are oppositely mated to one another such that the catch hook 78f on each gripper element 26f hooks over the pivot edge 80f on each gripper element 27f and vice versa. The hook 78f and edge 80f arrangement is designed such that the catch hooks 78f may only travel along the pivot edge 80f. The hooks 78f and pivot edges 80f are designed such that the gripper elements 26f and 27f are limited to being placed in either an open position (FIG. 7A) or a closed position (FIG. 7B).

Gripper elements 26f and 27f are preferably made from injection molded plastic, but could also be metal. The marker 10f is small such that it falls within the preferred range of sizes (described above) when in a closed position.

Turning now to FIGS. 8A–8E, an eighth embodiment of the present invention is shown in the form of a specimen marker 10i. Specimen marker 10i is similar to specimen marker 10d described above. Specimen marker 10i comprises a marker shell 110i and a gripper wire 84i.

As shown in FIGS. 8D and 8E, the marker shell 110i is designed similar to marker shell 110d (i.e. it includes front and back sections 112i and 114i which sandwich a core section 116i). The main differences are that the front and back sections 112i and 114i are square in shape and that the core 116i is polygonal with an outside edge defining a gripper wire holder 92i (rather than a pivot surface 86d) and that the specimen marker 10i is applied by bending the gripper wire 84i. The marker shell 110i is preferably made from injection molded plastic.

The gripper wire 84i is shaped such that it comprises a first gripper point 14i, an opposing second gripper point 12i, and tool grip areas 98i (see FIG. 8D). The gripper wire 84i is positioned around the wire holder 92i such that the gripper points 12i and 14i oppose each other. The gripper wire 84i is designed such that applying pressure at the tool grip areas 98i forces the gripper points 12i and 14i toward each other thereby causing the specimen marker 10i to proceed from an open position (FIG. 8A) to a closed position (FIG. 8B). Furthermore, as the gripper points 12i and 14i approach each other, a portion of a specimen may be pinched between or pierced by the gripper points 12i and 14i such that the specimen marker 10i may be attached to the specimen thereby marking it. The gripper wire 84i is preferably made from stainless steel wire having a diameter of approximately 0.015 inches.

Specimen marker 10i is small such that it falls within the preferred range of sizes (described above) when in a closed position.

A ninth embodiment of the present invention in the form of a specimen marker 10g is shown in FIGS. 9A–9E. Specimen marker 10g is similar to specimen marker 10i described above. Specimen marker 10g comprises a marker shell 110g and a gripper wire 84g.

As shown in FIGS. 9D and 9E, the marker shell 110g is designed similar to marker shell 110i (i.e. it includes front and back sections 112g and 114g which sandwich a core section 116g). The main difference is that the shape of the core 116g includes a circular section with a straight section extending therefrom (FIG. 9D). The core 116g includes an outside edge defining a gripper wire holder 92g (FIG. 9E) and a gripper wire stop 94g (FIG. 9D). The marker shell is preferably made from injection molded plastic.

The gripper wire 84g is shaped such that it comprises a first gripper point 14g, an opposing second gripper point 12g, a first gripper handle 18g, a second gripper handle 16g, and tool engagement holes 20g (associated with each gripper handle 16g and 18g). The gripper wire 84g is positioned on the wire holder 92g such that the gripper points 12g and 14g oppose each other. The gripper wire 84g is designed such that as the gripper handles 16g and 18g are held together, the gripper points 12g and 14g are held apart (FIG. 9A). Furthermore, as the gripper handles 16g and 18g move apart, the gripper points 12g and 14g move toward each other (FIG. 9B). As the gripper points 12g and 14g approach each other, a portion of a specimen may be pinched between or pierced by them such that the specimen marker 10g may be attached to the specimen thereby marking it. The gripper wire 84g is preferably made from spring-temper stainless steel wire having a diameter of approximately 0.015 inches.

The gripper wire 84g is further designed such that natural forces hold it in a closed position (as in FIG. 9B). However, the gripper wire 84g may be held in an open position (as in FIG. 9A) by a tool (not shown). When the specimen marker 10g is attached to a specimen, the tool merely releases the gripper wire 84g which allows the gripper wire 84g to then move to a closed position. The gripper wire stop 94g limits the position in which the tool may deflect the gripper wire 84g.

Specimen marker 10g is small such that it falls within the preferred range of sizes (described above) when in a closed position.

FIGS. 10A–10E show a tenth embodiment of the invention in the form of a specimen marker 10h. Specimen marker 10h comprises a front shell cover 22h, a rear shell cover 24h, and a gripper element 26h. As shown in FIG. 10C, the gripper element 26h is sandwiched between the front shell cover 22h and the rear shell cover 24h.

The gripper element 26h, as shown in FIG. 10D, comprises a first gripper point 14h, an opposing second gripper point 12h, a first gripper handle 18h, a second gripper handle 16h, tool holes 20h (one associated with each gripper handle 16h and 18h), pivot pin apertures 30h, and a gripper spring 96h. The gripper element 26h is designed such that as the gripper handles 16h and 18h are held together, the gripper points 12h and 14h are held apart (as in FIG. 10A). Furthermore, as the gripper handles 16h and 18h move apart, the gripper points 12h and 14h move toward each other (see FIG. 10B). As the gripper points 12h and 14h approach each other, a portion of a specimen may be pinched between or pierced by the points 12h and 14h such that the specimen marker 10h may be attached to a specimen thereby marking it. The gripper element 26h is preferably made by photo-etching spring-temper stainless steel.

The gripper element 26h is designed such that the gripper spring 96h causes the gripper element 26h to remain in a closed position (as in FIG. 10B). However, the gripper element 26h may be held in an open position (as in FIG. 10A) by a tool (not shown). When the specimen marker 10h is attached to a specimen, the gripper element 26h is released and the gripper spring 96h causes the gripper element 26h to move to a closed position (such that it may be attached to a specimen).

The shell covers 22h and 24h are generally square in shape having a flat top edge 25h. The shell covers 22h and 24h each include an inner surface 64h and 46h respectively and an outer surface 48h and 66h respectively. The shell covers 22h and 24h are preferably made from injection molded plastic.

As shown in FIG. 10D, the inner surface 46h of the rear shell cover 24h comprises gripper stop pins 32h and gripper pivot pins 34h (also see FIG. 10E). The gripper element 26h fits over and around these features of the rear shell cover 24h (FIG. 10D). The gripper element 26h is positioned between the shell covers 22h and 24h such that the gripper points 12h and 14h oppose each other and extend from the shell covers 22h and 24h at the flat edge 25h and the gripper handles 14h and 16h extend from the shell covers 22h and 24h at an edge opposite the flat edge 25h (FIGS. 10A–10E). The gripper stop pins 32h limit the gripper element 26h to a restricted range of motion (open and closed). The gripper pivot pins 34h provide points around which the gripper element 26h may pivot as it is moved from an open position to a closed position.

As shown in FIG. 10E, the shell covers 22h and 24h fit together. Specifically, the front shell cover 22h includes a pivot pin recess 40h and a stop pin recess 42h which respectively match and fit over the pivot pin 34h and the stop pin 32h of the rear shell cover 24h. These pin and recess couplings (34/40 and 32/42) allow the shell covers 22h and 24h to be fastened to each other (thereby sandwiching gripper element 26h).

The specimen marker 10h is small such that it falls within the preferred range of sizes (described above) when in a closed position.

An eleventh embodiment of the present invention in the form of a specimen marker 10j is shown in FIGS. 11A–11C. The specimen marker 10j comprises a specially designed gripper element 26j which is preferably made by photo-etching stainless steel.

The gripper element 26j includes a marker body 104j and two gripper arms 102j extending therefrom. The gripper arms 102j each include a gripper point 12j or 14j and a tool engagement hole 20j. The gripper arms 102j are each attached to the marker body 104j by means of a gripper hinge 100j and are positioned such that the gripper points 12j and 14j oppose each other.

A tool (not shown) is used to apply the specimen marker 10j to a specimen (not shown). The tool engages the tool holes 20j and is used to force the tool holes 20j together, thereby forcing the gripper arms 102j to approach the marker body 104j such that the gripper hinges 100j bend and the gripper points 12j and 14j move toward each other. This action forces the marker 10j from an open position (FIG. 11A) to a closed position (FIG. 11B). As the gripper points 12j and 14j approach each other, a portion of a specimen may be pinched between or pierced by the points 12j and 14j such that the specimen marker 10j attaches to the specimen thereby marking it. The closing action is similar to that used to close a staple.

The specimen marker 10j is small such that it falls within the preferred range of sizes (described above) when in a closed position.

A twelfth embodiment of the present invention in the form of a specimen marker 10k is shown in FIGS. 12A–12C. The specimen marker 10k comprises a specially designed gripper element 26k which is preferably made by photo-etching stainless steel.

The gripper element 26k is similar to gripper element 26j described above (i.e. including a marker body 104k with two gripper arms 102k extending therefrom each including a gripper point 12k or 14k and a tool hole 20k). The gripper arms 102k are each attached to the marker body 104k by means of a gripper hinge 100k and are positioned such that the gripper points 12k and 14k oppose each other.

A tool (not shown) is used to apply the specimen marker 10k to a specimen (not shown). The tool engages the tool holes 20k and is used to force the tool holes 20k together, thereby forcing the gripper arms 102k to approach the marker body 104k such that the gripper hinges 100k bend and the gripper points 12k and 14k move toward each other. This action forces the marker 10k from an open position (FIG. 12A) to a closed position (FIG. 12B). As the gripper points 12k and 14k approach each other, a portion of a specimen may be pinched between or pierced by the points 12k and 14k such that the specimen marker 10k attaches to the specimen thereby marking it.

The specimen marker 10k is small and flat such that it falls within the preferred range of sizes (described above) when in a closed position.

A thirteenth embodiment of the present invention in the form of a specimen marker 10l is shown in FIGS. 13A–13C. The specimen marker 10l comprises a specially designed gripper element 26l which is preferably made by photo-etching stainless steel.

The gripper element 26l includes a marker body 104l and two gripper arms 102l extending therefrom. The gripper arms 102l each include a gripper point 12l or 14l. The gripper arms 102l are each attached to the marker body 104l by means of a gripper hinge 100l and are positioned such that the gripper points 12l and 14l oppose each other. The gripper arms 102l are also attached to each other by means of a center hinge point 106l which defines a tool pressure point 108l. Another tool pressure point 108l is located on the marker body 104l.

The specimen marker 10l is designed such that a tool (not shown) is used to attach the specimen marker 10l to a specimen (not shown). The tool engages the tool pressure points 108l and is used to force the pressure points 108l together thereby forcing the center hinge 106l and the gripper hinges 100l to bend and the gripper points 12l and 14l to approach each other. This action forces the marker 10l from an open position (FIG. 13A) to a closed position (FIG. 13B), an action that includes an over-center snap action. As the gripper points 12l and 14l approach each other, a portion of a specimen may be pinched between or pierced by them such that the specimen marker 10l attaches to the specimen thereby marking it.

The specimen marker 10l is small and flat such that it falls within the preferred range of sizes (described above) when in a closed position.

Figure 14A:
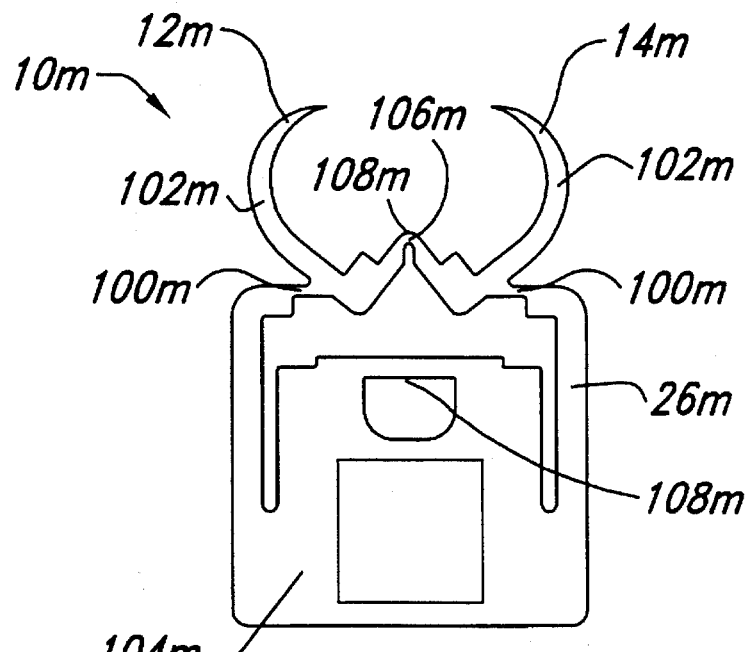
FIG. 14A is a plan view of a fourteenth embodiment of a specimen marker in an open position.
Figure 14B:
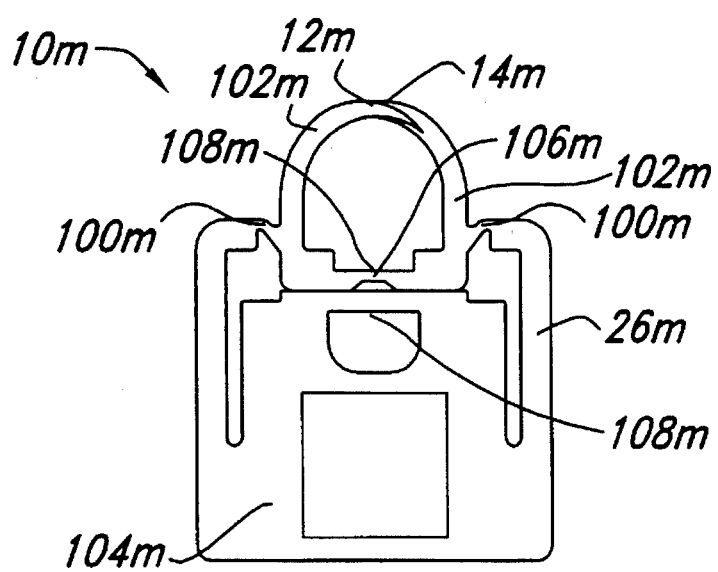
FIG. 14B is a plan view of the specimen marker of FIG. 14A in a closed position.
Figure 14C:
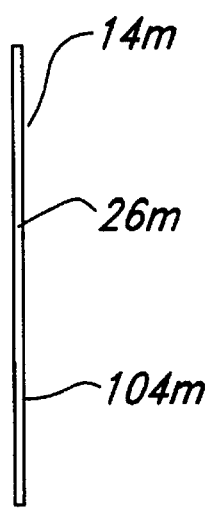
FIG. 14C is a side view of the specimen marker.

A fourteenth embodiment of the present invention in the form of a specimen marker 10m is shown in FIGS. 14A–14C. The specimen marker 10m comprises a gripper element 26m which is preferably made by photo-etching stainless steel.

The gripper element 26m includes a marker body 104m with two gripper arms 102m extending therefrom. The gripper arms 102m each include a gripper point 12m or 14m. The gripper arms 102m are each attached to the marker body 104m by means of a gripper hinge 100m and are positioned such that the gripper points 12m and 14m oppose each other. The gripper arms 102m are also attached to each other by means of a center hinge point 106m which defines a tool pressure point 108m. Another tool pressure point is located on the marker body 104m.

The specimen marker 10m is designed such that a tool (not shown) is used to attach the specimen marker 10m to a specimen (not shown). The tool engages the tool pressure points 108m and is used to force the pressure points 108m together thereby forcing the center hinge 106m and the gripper hinges 100m to bend and the gripper points 12m and 14m to approach each other. This action forces the marker 10m from an open position (FIG. 14A) to a closed position (FIG. 14B), an action that includes an over-center snap action. As the gripper points 12m and 14m approach each other, a portion of a specimen may be pinched between or pierced by them such that the specimen marker 10m is attached to the specimen thereby marking it.

The specimen marker 10m is small and flat such that it falls within the preferred range of sizes (described above) when in a closed position.

Turning now to FIGS. 15A–15E, a fifteenth embodiment of the present invention in the form of a specimen marker 10n is shown. The specimen marker 10n generally comprises a gripper element 26n and a slide member 152n.

FIGS. 15A and 15C–15E show the design of gripper element 26n. Gripper element 26n is a single piece of stainless steel which is shaped such that it generally comprises five sections: a front wall 154n, two back wall halves 156n, and two side walls 158n. The walls 154n, 156n and 158n are configured such that they together form a box-like structure which has an open top and bottom (FIG. 15D).

The front wall 154n comprises a plurality of tooth detents 162n (FIGS. 15A and 15E), an upper edge 160n with a tool pressure point 108n located thereon (FIG. 15A), and a lower edge 161n (FIG. 15E). The back wall halves 156n each include an inner edge 164n which has a plurality of gripper points 12n formed thereon (see FIG. 15E). The gripper element 26n is constructed such that the gripper points 12n of the inner edges 164n of the back wall halves 156n oppose each other (see FIGS. 15C and 15E). Each back wall half 156n is connected to one of the side walls 158n such that substantially ninety degree corners 168n are formed (FIGS. 15C and 15D). Each side wall 158n extends beyond the front wall 154n such that slide channels 166n are formed (FIGS. 15C and 15D). In addition, each side wall 158n connects to the front wall 154n such that gripper hinge corners 170n are formed (FIGS. 15C and 15D). The gripper element 26n is further constructed such that when the specimen marker 10n is in an open position (see FIGS. 15A, 15C, and 15E) the hinge corners 170n define a greater than ninety degree angle (see FIG. 15C) such that the opposing gripper points 12n are separated by an opening 180n (FIGS. 15C and 15E). Furthermore, when the specimen marker 10n is in a closed position (see FIGS. 15B and 15D) the hinge corners 170n define an angle of substantially ninety degrees (see FIG. 15D) such that the opposing gripper points 12n are not separated (FIG. 15D).

FIGS. 15A and 15B show the design of the slide member 152n. The slide member 152n is shaped such that it generally comprises a tetrahedron with a top edge 172n (FIGS. 15A and 15B) shorter than a bottom edge 174n (FIGS. 15A, 15B and 15E), a front surface 176n (FIGS. 15A and 15B) and a back surface 178n (FIG. 15E). The slide member 152n is constructed such that the bottom edge 174n includes a tool pressure point 108n (FIGS. 15A, 15B and 15E) and the back surface 178n includes a slide tooth 182n (FIGS. 15A, 15B (in phantom) and 15E).

The specimen marker 10n is generally supplied to the user in an open position (see FIGS. 15A, 15C, and 15E) with the opposing gripper points 12n separated by an opening 180n (see FIGS. 15C and 15E) and the slide member 152n positioned on the gripper element 26n such that the slide tooth 182n is engaged in the tooth detent 162n which is closest to the lower edge 161n of the front wall 154n of the gripper element 26n. The specimen marker 10n is attached to a specimen (not shown) by positioning the marker 10n on the specimen such that the portion of the specimen sought to be marked is located in the opening 180n between the opposing gripper points 12n. The user then forces the two tool pressure points 108n toward each other such that the slide member 152n slides along the slide channels 166n and the slide tooth 182n engages successive tooth detents 162n in the gripper element front wall 154n. The shape of the slide member 152n as it slides along the slide channels 166n forces the gripper hinge corners 170n to bend such that they approach substantially ninety degree angles (compare FIG. 15C and 15D). As the gripper hinge corners 170n approach ninety degree angles, the opposing gripper points 12n move toward each other such that a portion of a specimen desired to be marked may be pinched between or pierced by the opposing points 12n.

The specimen marker 10n is small such that it falls within the preferred range of sizes (described above) when in a closed position.

A sixteenth embodiment of the present invention in the form of a specimen marker 10p is shown in FIGS. 16A–16D. The specimen marker 10p comprises a gripper element 26p and a marker shell 110p.

As shown in FIGS. 16C and 16D, the marker shell 110p, although it is one molded piece, comprises three sections: a front section 112p, a back section 114p, and a core 116p. The front and back sections 112p and 114p sandwich the core 116p. The front and back sections 112p and 114p are substantially square in shape with top 118p, bottom 120p, and side 122p edges and include a tool pressure point 108p along the bottom edges 120p (FIG. 16A). The core 116p is shaped substantially like a triangle with a base 124p and two sides 126p which form an apex 128p (FIG. 16D). The core 116p is positioned such that its base 124p runs along the bottom edges 120p of the front and back sections 112p and 114p and its apex 128p reaches substantially to the top edges 118p of the front and back sections 112p and 114p. The core 116p also has a plurality of ridges 130p along its sides 126p thereby comprising a ratchet. The marker shell 110p is preferably made from injection molded plastic.

As shown in FIG. 16D, the gripper element 26p is shaped substantially like an "H" with two upright gripper arms 102p having top 136p and bottom 138p ends, and a cross-bar 140p having a top 142p and bottom 144p. The gripper element 26p comprises two upright gripper arms 102p, two opposing gripper points 12p and 14p (shaped like hooks and positioned at the top ends 136p of both upright arms 102p), two gripper pawls 146p (shaped like hooks and positioned at the bottom ends 138p of both upright arms 102p), a center hinge 106p (located at the top 142p of the "H" cross-bar 140p), and a tool pressure point 108p (located at the top 142p of the "H" cross-bar 140p). The gripper points 12p and 14p and the gripper pawls 146p all hook inward toward each other. The gripper element 26p is preferably made from stamped or photo-etched stainless steel.

The gripper element 26p is initially positioned such that the gripper pawls 146p are each engaged with a first set of ridges 130p on the sides 126p of the core 116p nearest to its apex 128p. Thus, the gripper pawls 146p are relatively close to each other (separated only by the width of the core 116p at its apex 128p). When the gripper pawls 146p are so engaged, the shape of the gripper element 26p is such that the gripper points 12p and 14p are in an open position (FIGS. 16A and 16D). When the gripper element 26p is so positioned, the specimen marker 10p is ready to use.

To attach the specimen marker 10p to a specimen a tool (not shown) engages the specimen marker 10p at the tool pressure point 108p on the gripper element 26p and the tool pressure point 108p on the bottom edge 120p of the marker shell 110p. The tool is then used to force the two pressure points 108p toward each other thereby forcing the gripper pawls 146p to engage successive ridges 130p down the sides 126p of the core 116p. The shape of the core 116p forces the gripper pawls 146p apart thereby causing the gripper arms 102p to pivot about the center hinge 106p and forcing the gripper points 12p and 14p to move toward each other and eventually reach a closed position (FIG. 16B). As the gripper points 12p and 14p approach each other, a portion of a specimen may be pinched between or pierced by the gripper points 12p and 14p such that the specimen marker 10p attaches to the specimen thereby marking it.

The specimen marker 10p is small and thin such that it falls within the preferred range of sizes (described above) when in a closed position.

A seventeenth embodiment of the present invention in the form of a specimen marker 10q is shown in FIGS. 17A–17D. The specimen marker 10q comprises a gripper element 26q and a marker shell 110q.

As shown in FIGS. 17A–17D, the marker shell 110q, although it is one molded piece, comprises three sections: a front section 112q, a back section 114q, and a core 116q. The front and back sections 112q and 114q sandwich the core 116q. The front and back sections 112q and 114q are substantially square in shape with top 118q and bottom 120q edges and include a tool pressure point window 148q within which is located a tool pressure point 108q. The core 116q is hexagonal and is shaped substantially like an arrow with a flat point including a base 124q which connects two straight sides 150q which connect to two angled sides 126q which in turn connect to a flat apex edge 128q. The core 116q is positioned such that its base 124q runs along the bottom edges 120q of the front and back sections 112q and 114q, and its flat apex edge 128q reaches substantially to the top edges 118q of the front and back sections 112q and 114q. The core 116q also has two sets of ridges 130q, one set of ridges 130q at the point where the angled sides 126q meet the flat apex edge 128q and another set of ridges 130q at the point where the angled sides 126q meet the straight sides 150q, thereby comprising a ratchet. The marker shell 110q is preferably made from injection molded plastic.

As shown in FIG. 17D, the gripper element 26q is shaped substantially like an "H" with two upright gripper arms 102q having top 136q and bottom 138q ends, and a cross-bar 140q having a top 142q and bottom 144q. The gripper element 26q comprises two gripper arms 102q, two opposing gripper points 12q and 14q (shaped like hooks and positioned at the top ends 136q of both upright arms 102q), two gripper pawls 146q (shaped like hooks and positioned at the bottom ends 138q of both upright arms 102q), a center hinge 106q (located at the top 142q of the "H" cross-bar 140q), and a tool pressure point 108q (located at the top 142q of the "H" cross-bar 140q). The gripper points 12q and 14q and the gripper pawls 146q all hook inward toward each other. The gripper element 26q is preferably made from photo-etched stainless steel.

The gripper element 26q is initially positioned such that the gripper pawls 146q are each engaged to a first set of ridges 130q located at the point where the angled sides 126q meet the flat apex edge 128q. Thus, the gripper pawls 146q are relatively close to each other (separated only by the width of the core 116q at its flat apex 128q). When the gripper pawls 146q are so engaged, the shape of the gripper element 26q is such that the gripper points 12q and 14q are in an open position, as shown in FIG. 17A. When the gripper element 26q is so positioned, the specimen marker 10q is ready to use.

To attach the specimen marker 10q to a specimen, a tool (not shown) engages the specimen marker 10q at the tool pressure points 108q. The tool is then used to force the two pressure points 108q toward each other thereby forcing the gripper pawls 146q to engage the second set of ridges 130q at the point where the angled sides 126q meet the straight sides 150q of the core 116q. Simultaneously, the shape of the core 116q forces the gripper pawls 146q apart thereby causing the gripper arms 102q to pivot about the center hinge 106q and forcing the gripper points 12q and 14q to move toward each other and eventually reach a closed position as shown in FIG. 17B. As the gripper points 12q and 14q approach each other (and the specimen marker approaches a closed position), a portion of a specimen may be pinched between or pierced by the gripper points 12q and 14q such that the specimen marker 10q attaches to the specimen thereby marking it.

The specimen marker 10q is small and thin such that it falls within the preferred range of sizes (described above) when in a closed position.

An eighteenth embodiment of the present invention is shown in FIGS. 18A–18D in the form of a specimen marker 10r. Specimen marker 10r generally comprises a specially designed gripper element 26r which is preferably made from injection molded plastic.

The gripper element 26r is very similar to gripper element 26j described above (i.e. gripper element 26r includes a marker body 104r and two gripper arms 102r each including a gripper point 12r or 14r and a tool engagement hole 20r). The main difference is that the gripper arms 102r are both restricted in their movement by a ratchet mechanism (described below).

The gripper arms 102r are each attached to the marker body 104r by means of a gripper hinge 100r and are positioned such that the gripper points 12r and 14r oppose each other (FIGS. 18A and 18B). A tool (not shown) is used to apply the specimen marker 10r to a specimen. The tool engages the tool engagement holes 20r and is used to force the tool holes 20r together, thereby forcing the gripper arms 102r to approach the marker body 104r such that the gripper hinges 100r bend and the gripper points 12r and 14r move toward each other. This action forces the marker 10r from an open position (FIG. 18A) to a closed position (FIG. 18B). As the points 12r and 14r approach each other, a portion of a specimen may be pinched between or pierced by the points 12r and 14r such that the specimen marker 10r attaches to the specimen thereby marking it.

As mentioned above, the movement of each gripper arm 102r is limited by a ratchet mechanism comprising a ratchet member 184r and a ratchet engagement tooth 186r. The ratchet member 184r comprises a ratchet fin 188r extending from each gripper arm 102r toward the marker body 104r (FIG. 18A), a plurality of ratchet ridges or teeth 190r located upon each ratchet fin 186r (FIGS. 18A and 18D), and two ratchet engagement teeth 186r positioned on the marker body 104r such that the engagement teeth 186r engage the ratchet ridges 190r on the ratchet fins 188r as the gripper arms 102r are forced together (FIG. 18D).

The movement of the gripper arms 102r is further limited by a set of alignment tabs 192r located on the marker body 104r (FIG. 18A). The alignment tabs 192r are designed and positioned such that they engage the tool engagement holes 20r at a point where the specimen marker 10r is in a fully closed position (FIG. 10B). Thus, when the marker 10r is attached to a specimen, the alignment tabs 192r cause the marker 10r to remain in a closed position by retaining the tool engagement holes 20r as shown in FIG. 18B.

The specimen marker 10r is small such that it falls within the preferred range of sizes (described above) when in a closed position.

A nineteenth embodiment of the present invention is shown in FIGS. 19A–19E in the form of a specimen marker 10s. Specimen marker 10s generally comprises a specially designed gripper element 26s which is preferably made from injection molded plastic. The specimen marker 10s is similar in shape, design, and dimensions to specimen marker 10r (described above).

The specimen marker 10s is very similar to specimen marker 10r described above (i.e. specimen marker 10s comprises a gripper element 26s which includes a marker body 104s with ratchet engagement teeth 186s and alignment tabs 192s, two gripper arms 102s each including a gripper point 12s or 14s, a tool engagement hole 20s, and a ratchet fin 188s with a plurality of ratchet teeth 190s). The main difference is the design of the gripper points 12s and 14s compared to gripper points 12r and 14r. As shown in FIG. 18C, the features of marker 10r generally occur in the same spacial plane. However, as shown in FIGS. 19C–19E, gripper points 12s and 14s extend out of the spacial plane for the other features of marker 10s.

Although the gripper points 12s and 14s are designed slightly differently, the specimen marker 10s attaches to a specimen in the same way as specimen marker 10r (described above). In addition, the specimen marker 10s is small such that it falls within the preferred range of sizes (described above) when in a closed position.

A twentieth embodiment of the present invention is shown in FIGS. 20A–20D in the form of a specimen marker 10t. The specimen marker 10t generally comprises a movable gripper element 26t and a marker body 104t including a stationary gripper point 12t. Specimen marker 10t is preferably made from injection molded plastic (although it, or parts of it, could be made from metal, preferably stainless steel).

As shown in FIG. 20D, movable gripper element 26t is shaped like a "6" comprising an arm 102t with a top end 136t and a curved bottom end 138t. The gripper element 26t comprises a gripper point 14t and a tool pressure point 108t at the top end 136t, a pivot pin edge 31t, a gripper pawl 146t, and a gripper stop tab 194t at the bottom end 138t.

The specimen marker 10t also comprises a marker body 104t. The design of the marker body 104t is shown in FIGS. 20A–20D. The marker body 104t generally comprises a stationary gripper point 12t, a tool pressure point 108t, a gripper pivot pin 34t, and a gripper stop tab 194t. The pivot pin 34t is designed such that the gripper element 26t movably fits around the pivot pin 34t. In addition, the pivot pin 34t includes gripper holder tabs 196t (FIGS. 20C and 20D) which movably hold the gripper element 26t on the pivot pin 34t such that the pivot pin edge 31t is in contact with the pivot pin 34t. Furthermore, the pivot pin 34t includes a plurality of ratchet teeth 190t such that the gripper pawl 146t engages the ratchet teeth 190t (FIG. 20D) as the gripper element 26t rotates around the pivot pin 34t.

The specimen marker 10t is attached to a specimen by a tool engaging the tool pressure points 108t and forcing them toward each other (from an open position, FIG. 20A, to a closed position, FIG. 20B). This action causes the gripper element 26t to rotate around the pivot pin 34t and the gripper points 12t and 14t to approach each other such that a portion of a specimen may be pinched between or pierced by them thereby attaching the specimen marker 10t thereto. The movement causes the gripper pawl 146t to engage successive ratchet teeth 190t in the pivot pin 34t such that the specimen marker 10t is held in a closed position (FIG. 20B) once it is attached to a specimen.

The gripper stop tabs 194t are designed to limit the gripper element 26t rotation such that the distance between the gripper points 12t and 14t is restricted.

The specimen marker 10t is small such that it falls within the preferred range of sizes (described above) when in a closed position.

FIGS. 21A–21I show a twenty-first embodiment of the present invention in the form of a specimen marker 10u and a marker tool 198u. The specimen marker 10u generally comprises two flat gripper elements 26u and 27u (shown in FIG. 21D), a front shell cover 22u and a rear shell cover 24u (see FIG. 21C). The marker tool 198u generally comprises two tool elements 200u and a tool pivot 202u (FIGS. 21F–21I).

FIG. 21D shows the design of the gripper elements 26u and 27u. Both gripper elements 26u and 27u are of the same design and shape shown, they are merely oppositely placed between the shell covers 22u and 24u. As FIG. 21D shows, gripper element 27u includes gripper point 12u, pivot pin aperture 30u, tool contact 204u, and a stop pin detent 220u. FIG. 21D also shows that gripper element 26u includes gripper point 14u, pivot pin aperture 30u (not shown), a tool contact 204u, and a stop pin detent 220u. The gripper elements 26u and 27u are preferably made by photo-etching stainless steel.

Each specimen marker 10u also comprises a front shell cover 22u and a rear shell cover 24u between which the gripper elements 26u and 27u are movably sandwiched (FIG. 21C). The shell covers 22u and 24u are generally square in shape each including a bottom edge 23u, a top edge 25u, an inner surface 64u (FIG. 21E) and 46u (FIGS. 21D and 21E) respectively, and an outer surface 48u (FIG. 21A) and 66u (FIG. 21E) respectively. The shell covers 22u and 24u are preferably made from injection molded plastic.

As shown in FIG. 21D, the inner surface of the rear shell cover 24u comprises several stop pins 32u, a pivot pin 34u, and a tool retention groove 206u. The gripper elements 26u and 27u fit over and around these features of the rear shell cover 24u (FIG. 21D) and are positioned between the shell covers 22u and 24u such that the gripper points 12u and 14u protrude out from the top edges 25u of the shell covers 22u and 24u opposing each other.

As shown in FIG. 21E, the shell covers 22u and 24u complement each other. The inner surface 64u of the front shell cover 22u is adapted to match the features of the rear shell cover 24u. Specifically the front shell cover 22u includes a pivot pin recess 40u and stop pin recesses 42u (only one is shown) which match and fit over the pivot pin 34u and the stop pins 32u of the rear shell cover 24u respectively. In addition, the shell covers 22u and 24u fit together to form a tool insert gap 208u near the bottom edges 23u of the shell covers 22u and 24u. The tool insert gap 208u provides an entry for the marker tool 198u (described below).

As shown in FIGS. 21A and 21B, the front shell cover 22u includes two windows 210u through which a user can view the gripper elements 26u and 27u.

FIGS. 21F–21I show the design of the marker tool 198u. The marker tool 198u comprises a tool pivot 202 and two tool elements 200u which each include a tool cam 212u, a retention bump 214u, a tool handle 216u, and a finger hole 218u. The tool 198u is designed such that as the tool handles 216u are moved toward each other, the tool cams 212u move away from each other, and vice versa (compare FIG. 21F to FIG. 21I).

FIGS. 21F–21I show the three steps of forcing a specimen marker 10u from an open position (FIGS. 21A, 21F and 21G) to a closed position (FIGS. 21B, 21H and 21I) such that it may be attached to a specimen. First, the marker tool 198u is inserted into the tool insert gap 208u of the marker shell covers 22u and 24u (FIGS. 21F and 21G). When the marker tool 198u is properly inserted, the tool cams 212u touch the tool contacts 204u of the gripper elements 26u and 27u and the tool retention bumps 214u engage the tool retention grooves 206u of the shell covers 22u and 24u.

Second, the tool handles 216u are moved toward each other (FIGS. 21G and 21H) thereby forcing the tool cams 212u away from each other thereby forcing the tool contacts 204u away from each other. This action causes the gripper element 26u to rotate counter clock-wise and the gripper element 27u to rotate clock-wise around the pivot pin 34u (see FIG. 21D). As a result, the gripper points 12u and 14u move toward each other such that a portion of the specimen desired to be marked may be pinched between or pierced by the points 12u and 14u such that the marker 10u attaches to the specimen.

Third, the tool 198u is removed from the marker 10u, leaving the marker 10u attached to a specimen.

Turning back to FIG. 21D, when a marker 10u is placed onto a specimen, as described above, the gripper elements 26u and 27u rotate around the pivot pin 34u. However, the stop pins 32u limit the rotations of the gripper elements 26u and 27u to a position where the gripper points 12u and 14u meet (as shown in FIG. 21B). In addition, the stop pin detents 220u engage the stop pins 32u such that the gripper elements 26u and 27u remain in a closed position (as in FIG. 21B).

The specimen marker 10u is small such that it falls within the preferred range of sizes (described above) when in a closed position.

FIGS. 22A–22B show a twenty-second embodiment of the present invention in the form of a specimen marker 10v and a marker tool 198v. Specimen marker 10v is very similar to specimen marker 10u. The only differences are the shape of the gripper elements 26v and 27v (almost the same as 26u and 27u), that there are two pivot pins 34v (rather than just one pivot pin 34u), and that there are no windows 210u in the marker shell covers 22v and 24v. Marker tool 198v is very similar to marker tool 198u. The only differences are the design of the tool pivot 202v and the design of the tool handles 216v (no finger holes 218u). Otherwise, the features and the manipulation of the specimen marker 10v and the marker tool 198v are the same as specimen marker 10u and marker tool 198u.

The specimen marker 10v is small such that it falls within the preferred range of sizes (described above) when in a closed position.

FIGS. 23A–23I show a twenty-third embodiment of the present invention in the form of a specimen marker 10w and a marker tool 198w. Specimen marker 10w is very similar to specimen marker 10u. The differences include the shape of the gripper elements 26w and 27w (almost the same as 26u and 27u), that there are two pivot pins 34w (rather than just one pivot pin 34u), that there are only two stop pins 32w (rather than three stop pins 32u), and that there are no windows 210u in the shell covers 22w and 24w.

The differences in the shapes of the gripper elements 26w and 27w include the feature of a gripper cross-over retainer 222w (see FIG. 23D). The cross-over retainer 222w is needed in this embodiment because the gripper elements 26w and 27w are on different and separate pivot pins 30w and the cross-over retainer 222w keeps the gripper elements 26w and 27w in corresponding positions.

In addition to having two pivot pins 30w and only two stop pins 32w, the difference in the shapes of the shell covers 22w and 24w includes the aspect that the tool retention groove 206w is located on the outer surface 48w of the rear shell cover 24w (FIG. 23E).

Although the marker tool 198w is different than the marker tool 198u, they both perform the same function. Marker tool 198w includes a tool cam 212w, a tool retention bump 214w, a marker holder area 224w, a tool slide 226w, and a tool body 228w (FIGS. 23F–23I).

FIGS. 23F–23I show the three steps of forcing a specimen marker 10w from an open position (FIGS. 23A, 23F and 23G) to a closed position (FIGS. 23B, 23H and 23I) such that it may be attached to a specimen. First, a specimen marker 10w is placed onto the marker holder area 224w of the marker tool 198w (FIGS. 23F and 23G). When the marker 10w is properly positioned on the marker holder area 224w, the tool retention bump 214w engages the tool retention groove 206w of the shell cover 24w.

Second, the tool slide 226w is moved toward the specimen marker 10w (FIGS. 23G and 23H) thereby forcing the tool cam 212w into the tool insert gap 208w of the marker 10w such that the tool contacts 204w are forced away from each other. This action causes the gripper element 26w to rotate counter clock-wise and the gripper element 27w to rotate clock-wise around their respective pivot pins 34w (see FIG. 23D). As a result, the gripper points 12w and 14w move toward each other such that a portion of the specimen desired to be marked may be pinched between the points 12w and 14w such that the marker 10w attaches to the specimen. The marker 10w is held in the closed position by an over-center action produced by the cross-over retainer.

Third, the tool 198w is removed from the marker 10w, automatically releasing the market 10w, and leaving it 10w attached to a specimen (FIG. 23I).

The specimen marker 10w is small such that it falls within the preferred range of sizes (described above) when in a closed position.

A twenty-fourth embodiment of the present invention is shown in FIGS. 24A–24F in the form of a specimen marker 10x. The specimen marker 10x generally comprises a gripper element 26x and a marker shell 110x.

Each specimen marker 10x includes a gripper element 26x which generally comprises a hook shaped wire having a gripper point 12x (FIGS. 24A and 24B), a gripper shaft 230x (FIGS. 24A, 24B, and 24D), and a gripper shaft head 232x (FIGS. 24A, 24B, and 24D).

Each specimen marker 10x also includes a marker shell 110x which is generally rectangular in shape having a top edge 25x and a bottom edge 23x (see FIGS. 24A–24D) and preferably made from injection molded plastic. The marker shell 110x also includes an inner surface 238x (FIGS. 24D–24F) and an outer surface 240x (FIGS. 24A–24C and 24E–24F). The marker shell 110x generally comprises three areas: a front shell cover 22x (FIGS. 24B–24F), a rear shell cover 24x (FIGS. 24A, and 24C–24F), and a shell hinge area 234x (FIGS. 24A–24F) connecting the shell covers 22x and 24x.

The marker shell 110x includes a plurality of retainer pins 38x (FIGS. 24A and 24D–24F) located on the inner surface 238x of the front shell cover 22x and a plurality of matching retainer pin apertures 36x (FIGS. 24A and 24D–24E) located on the inner surface 238x of the rear shell cover 24x. The marker shell 110x also includes a gripper pivot area 236x (FIGS. 24C–24F and, shown in phantom, FIG. 24B) located on the inner surface 238x of the shell hinge area 234x (see FIGS. 24E–24F). In addition, the marker shell 110x includes two gripper point slots 242x located on the inner surface 238x of the shell covers 22x and 24x at the top edge 25x (FIGS. 24A–24F).

The marker shell 110x is designed such that the shaft 230x of the gripper element 26x is placed along the gripper pivot area 236x of the inner surface 238x of the hinge 234x such that the gripper point 12x projects out over the top edge 25x of the marker shell 110x (FIGS. 24A, 24B, and 24D) and the gripper shaft head 232x extends out beyond the bottom edge 23x of the marker shell 110x (FIGS. 24A, 24B, and 24D). To assemble the specimen marker 10x, the marker shell 110x is folded in half along the hinge 234x such that the hinge area 234x wraps around the gripper shaft 230x with the gripper pivot area 236x in direct contact with the shaft 230x (FIG. 24E) and the retainer pins 38x on the front cover 22x engage the retainer pin apertures 36x on the rear cover 24x (FIG. 24E).

The assembled marker 10x (FIGS. 24A–24C) is attached to a specimen (not shown) by piercing the gripper point 12x through the specimen tissue surface and securing the gripper point 12x into the gripper point slot 242x which retains the gripper point 12x in a closed position (FIG. 24B). The gripper element 26x is preferably made from stainless steel wire.

The specimen marker 10x is small such that it falls within the preferred range of sizes (described above) when in a closed position.

FIGS. 25A–25F show a twenty-fifth embodiment of the present invention in the form of a specimen marker 10y. The specimen marker 10y generally comprises a gripper element 26y (FIGS. 25C–25D) and a marker shell 110y (FIGS. 25A–25D).

FIGS. 25C and 25D show the design of gripper element 26y. As shown, the gripper element 26y comprises a straight shaft 230y with an arrow element 244y on both ends. One arrow element 244y comprises a gripper point 12y and two gripper barbs 246y (FIGS. 25A–25D) and the other arrow element 244y comprises a gripper point 12y and two retainer barbs 248y (FIGS. 25C and 25D). The shaft 230y includes two tool engagement areas 20y (FIGS. 25A–25D), a set of tool restraints 250y (FIGS. 25A–25D), and a set of gripper restraints 252y (FIGS. 25C–25D). As shown in FIG. 25D, the features of the gripper element 26y all occur in a single plane except the gripper barbs 246y and the retainer barbs 248y which extend out from that plane.

FIGS. 25C and 25D show the design of the marker shell 110y. As shown, the marker shell 110y comprises a gripper element insert slot 254y (FIGS. 25B–25D). The gripper element insert slot 254y comprises a retainer barb stop 256y (FIGS. 25C and 25D) and a gripper restraint stop 258y (FIG. 25C).

As shown in FIGS. 25C and 25D, the gripper element 26y is inserted in the gripper element insert slot 254y such that one arrow element 244y is positioned within the marker shell 110y with retainer barbs 248y placed beyond the retainer barb stop 256y. As shown in FIG. 25C, the gripper restraint stop 258y limits the extent that the gripper element 26y can be inserted into the marker shell 110y. In addition, the retainer barbs 248y and retainer barb stop 256y limit the extent that the gripper element 26y can be withdrawn from the marker shell 110y. Thus, the marker shell 110y is held onto the gripper element 26y, and vice versa.

A tool (not shown), such as forceps, is used to attach the specimen marker 10y to a specimen tissue surface 260y (FIG. 25A). Generally, a consumer uses the tool to engage the specimen marker 10y at the tool engagement areas 20y and to force the gripper point 12y into the specimen tissue surface 260y. The gripper point 12y is forced into the tissue surface 260y such that the gripper barbs 246y are placed beyond the tissue surface 260y but the tool restraints 250y are not (see FIG. 25A). The gripper barbs 246y limit the extent that the gripper element 26y (and, therefore, the specimen marker 10y) can be withdrawn from the specimen tissue 260y and the tool restraints 250y limit the extent that the gripper element 26y can be inserted into the specimen tissue 260y. Thus, the specimen marker 10y is held onto the specimen, and vice versa.

As shown in FIGS. 25E and 25F, the specimen markers 10y can be provided to the consumer in marker holder packaging 52y similar to the marker holder packaging 50 (described above). As with specimen marker 10 and marker holder packaging 50, the specimen markers 10y are removably attached to the packaging 52y. The main difference in holder packaging 52y is that the marker shells 110y are not manufactured contemporaneously with and attached to the holder packaging 52y. Rather, a set of gripper elements 26y are formed from a sheet of metal such that the gripper elements 26y are still attached to a metal web 264y and the metal web 264y is then attached to the holder packaging 52y by means of web retainers 266y (FIG. 25E). An additional difference is that packaging 52y comprises a single holder tray 262y with an optional cover sheet 54y (FIG. 25F).

The specimen marker 10y is small such that it falls within the preferred range of sizes (described above) when in a closed position.

While several embodiments of the present invention have been shown and described, various modifications may be made without departing from the scope of the present invention, and all such modifications and equivalents are intended to be covered.

What is claimed is:

1. A pathology tissue specimen marker for attaching to and thereby marking tissue specimens to aid in orienting or identifying the tissue specimens comprising two gripper elements each having
      a body section with a pivot pin aperture which allows the gripper elements to attach to and rotate around at least one pivot pin,
      a head section extending from said body section comprising a point, and
      a tail section extending from said body section in an opposite direction as said head section comprising a handle which has a tool engagement hole located therein, and
   two marker shell covers providing said pivot pin which fits the apertures in the body sections of said gripper elements such that said gripper elements may movably attach between said covers and rotate around said pivot pin, said shell covers being proportioned to fit over and cover said body sections of said gripper elements so as to conceal the apertures in the body sections of said gripper elements.

2. The specimen marker of claim 1 wherein the two gripper elements attach to and are positioned on the marker shells such that
   the point of each gripper element opposes the point of the other gripper element and
   as said gripper elements are rotated the point of each approaches the other such that a portion of a tissue specimen may be caught between the points.

3. The specimen marker of claim 1 wherein the marker shell covers are configured to provide a stop pin and the body sections of the gripper elements are each configured to provide a stop pin slot through which the stop pin is adapted to fit, and said stop pin and stop pin slots are adapted to restrict the rotations of the gripper elements.

4. The specimen marker of claim 3 wherein the stop pin slots of the gripper elements are configured to have first widths Which enable the stop pin to slidably move therein and said slots are configured to have enlarged areas which have second widths which are larger than the first widths of said slots such that the gripper elements remain in positions where the stop pin is located in one of the enlarged areas of the slots.

5. The specimen marker of claim 1 wherein the specimen marker may removably attach to a marker support frame.

6. A pathology tissue specimen marker kit comprising a pathology tissue specimen marker including a pair of gripper elements each having a body section with an aperture, a head section extending from said body section comprising a point, and a tail section extending from said body section in an opposite direction as said head section comprising a tool engager, and a marker shell having a pivot pin which fits the apertures of the body sections of the pair of gripper elements whereby said gripper elements may movably attach to said marker shell and rotate around said pivot pin, and a tool which engages the tool engagers and which when manipulated forces the gripper elements to rotate about the pivot causing the points to move toward each other and thereby attach the marker to a specimen.

* * * * *